(12) United States Patent
McGuckin, Jr.

(10) Patent No.: US 8,210,410 B2
(45) Date of Patent: Jul. 3, 2012

(54) SURGICAL APPARATUS AND METHOD

(76) Inventor: James F. McGuckin, Jr., Villanova, PA (US)

( * ) Notice: Subject to any disclaimer, the term of this patent is extended or adjusted under 35 U.S.C. 154(b) by 52 days.

(21) Appl. No.: 11/747,948

(22) Filed: May 14, 2007

(65) Prior Publication Data

US 2007/0213743 A1  Sep. 13, 2007

Related U.S. Application Data

(63) Continuation of application No. 09/697,306, filed on Oct. 27, 2000, now Pat. No. 7,235,089, which is a continuation of application No. 08/988,052, filed on Dec. 10, 1997, now Pat. No. 6,264,086, which is a continuation of application No. 08/352,325, filed on Dec. 7, 1994, now Pat. No. 5,868,760.

(51) Int. Cl.
*A61B 17/068* (2006.01)
(52) U.S. Cl. .................................................. 227/175.1
(58) Field of Classification Search .............. 227/175.1, 227/180.1, 181.1; 606/144, 148, 150, 142
See application file for complete search history.

(56) References Cited

U.S. PATENT DOCUMENTS

| | | | | | |
|---|---|---|---|---|---|
| 3,193,165 | A | * | 7/1965 | Akhalaya et al. | 227/8 |
| 4,473,077 | A | * | 9/1984 | Noiles et al. | 227/179.1 |
| 4,681,107 | A | * | 7/1987 | Kees, Jr. | 606/142 |
| 5,170,925 | A | * | 12/1992 | Madden et al. | 227/175.1 |
| 5,251,611 | A | * | 10/1993 | Zehel et al. | 600/141 |

* cited by examiner

*Primary Examiner* — Ryan Severson
(74) *Attorney, Agent, or Firm* — Fay Kaplun & Marcin, LLP

(57) ABSTRACT

Surgical method and apparatus for resectioning tissue, preferably lumenal tissue, with a remaining portion of an organ being anastomized with staples or other fastening means, preferably endolumenally. The apparatus may be inserted via a naturally occurring body orifice or a surgical incision and then advanced using either endoscopic or radiological imaging guidance to an area where surgery is to be performed. Under endoscopic or diagnostic imaging guidance the apparatus is positioned so tissue to be resected is manipulated into an inner cavity of the apparatus. The apparatus then cuts the diseased tissue after stapling and retains the diseased tissue within the apparatus. The rent resulting in a border of healthy tissue is anastomosed with surgical staples.

15 Claims, 14 Drawing Sheets

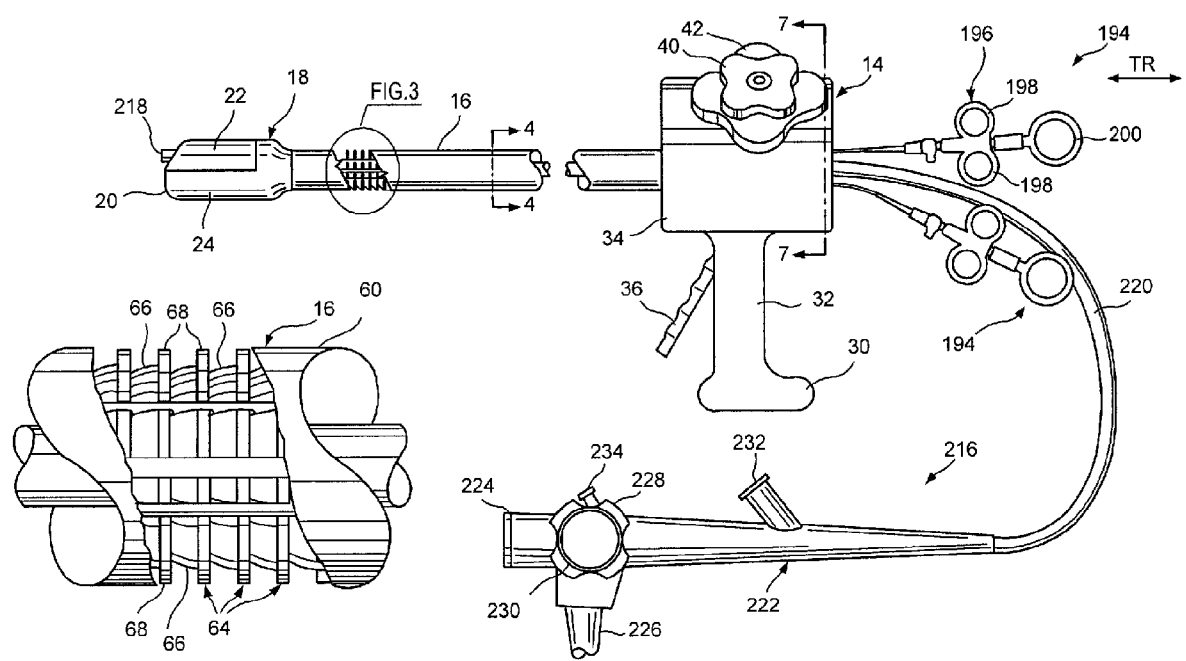

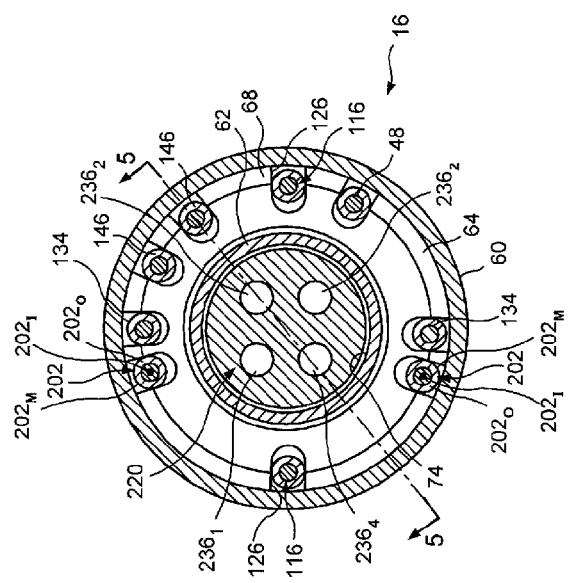
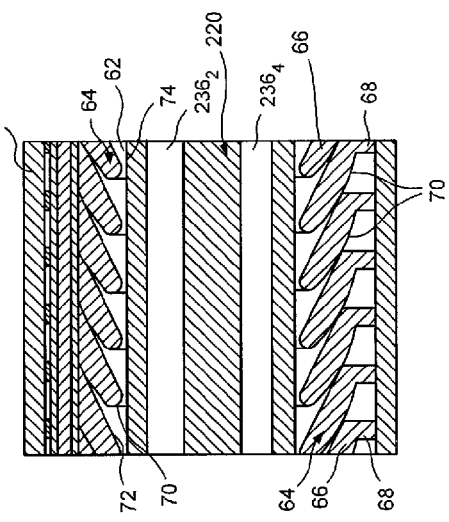

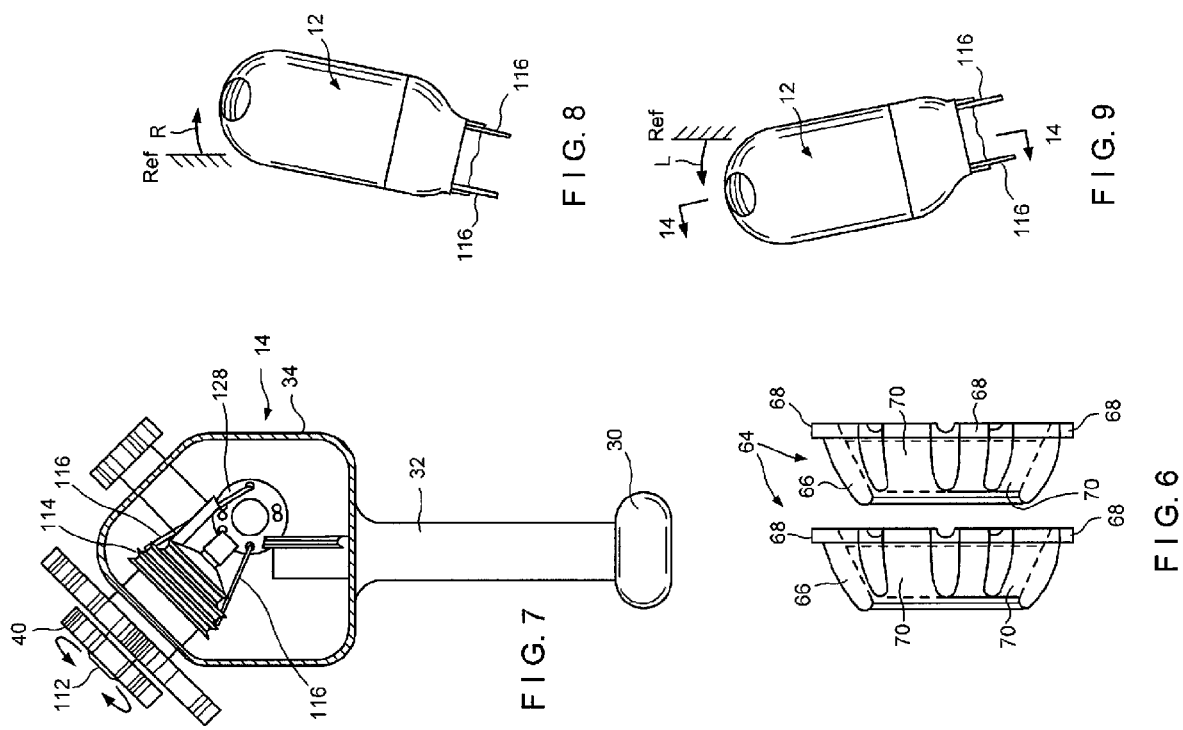

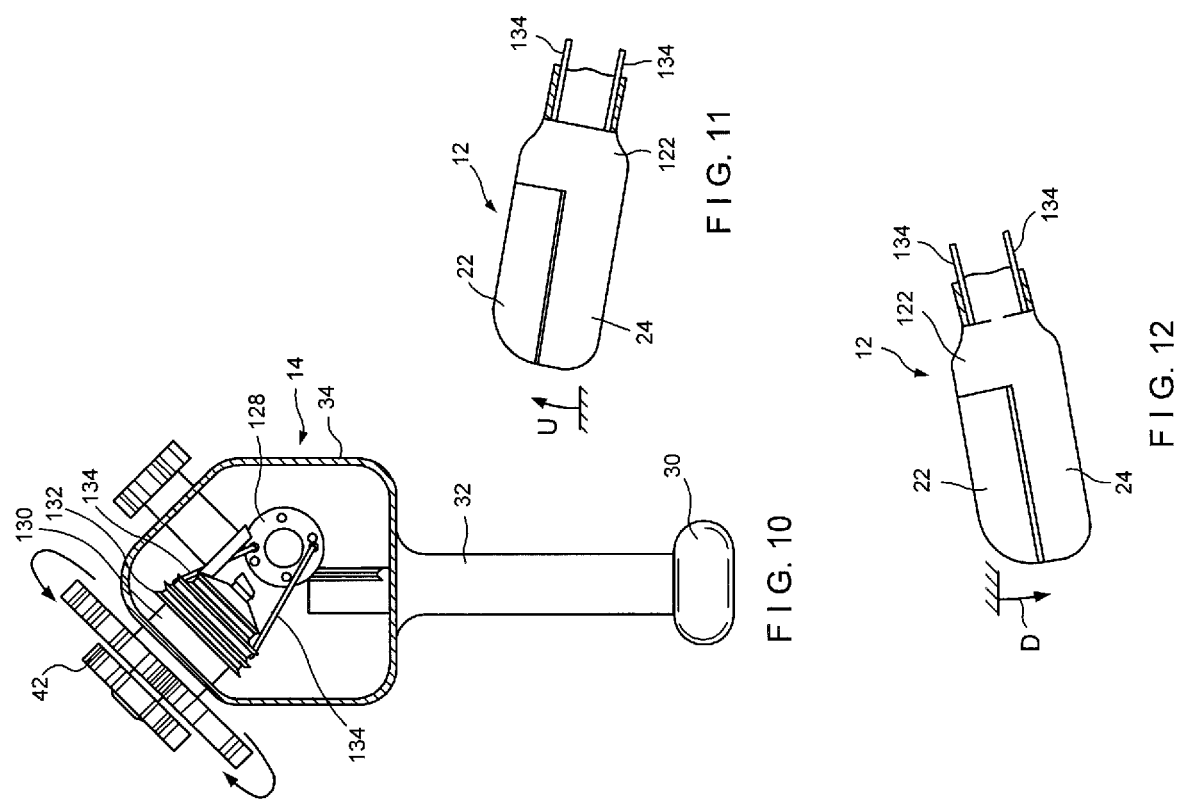

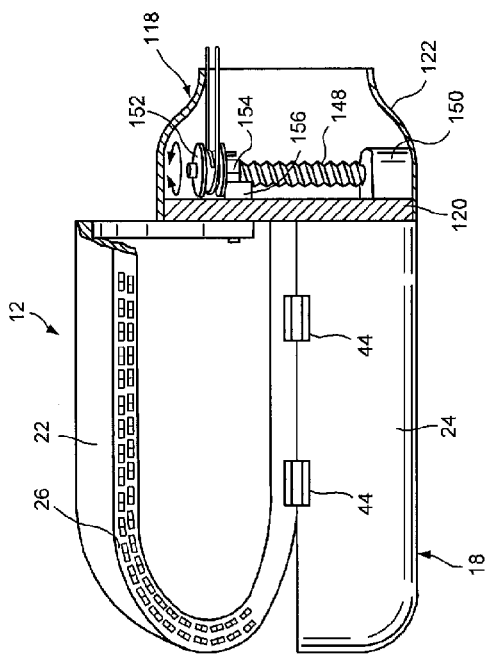
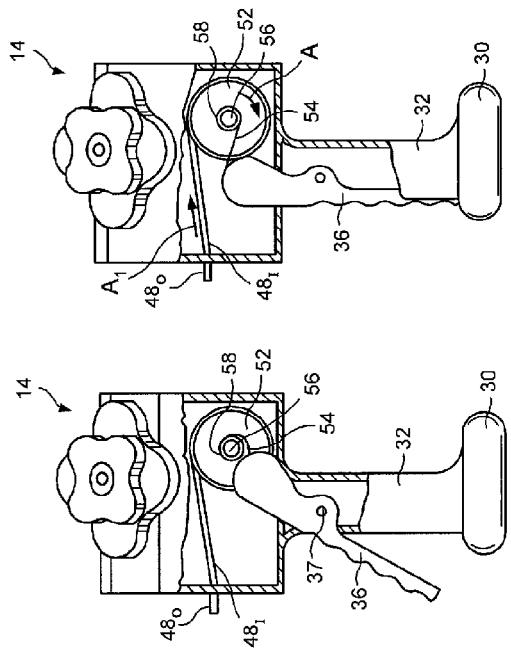
FIG. 15
FIG. 16
FIG. 17

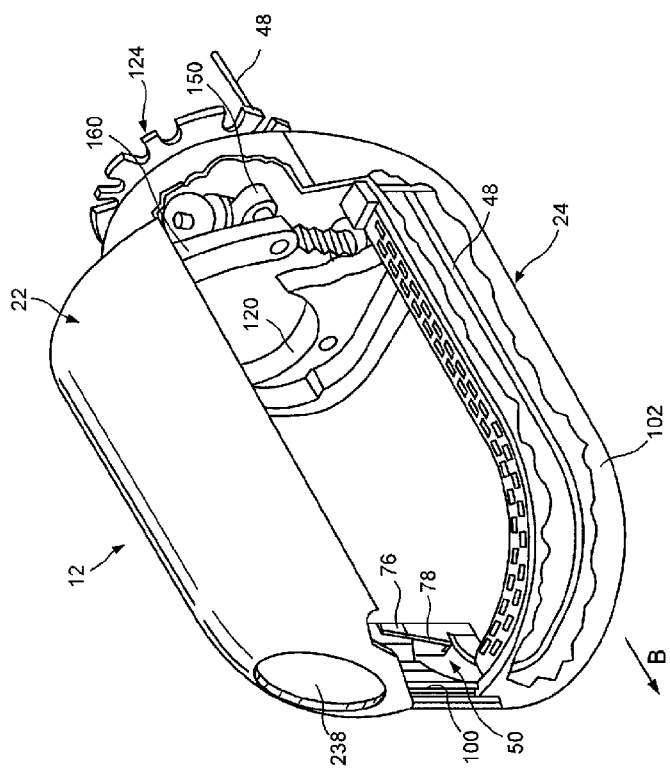
F I G. 18
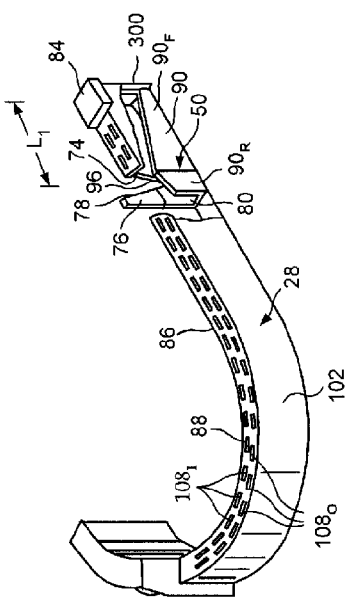
F I G. 19

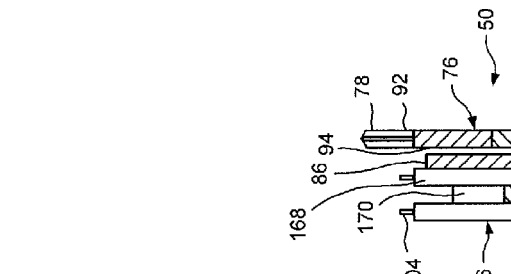
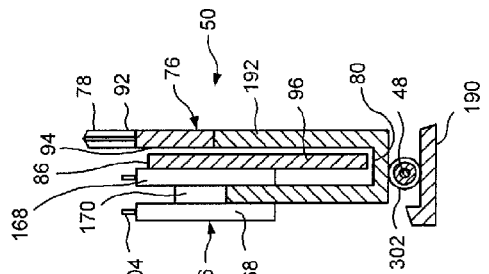
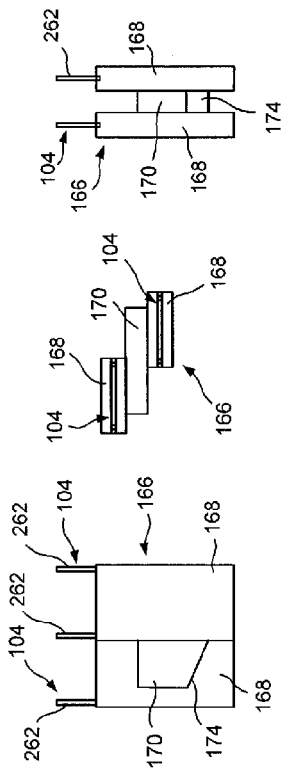
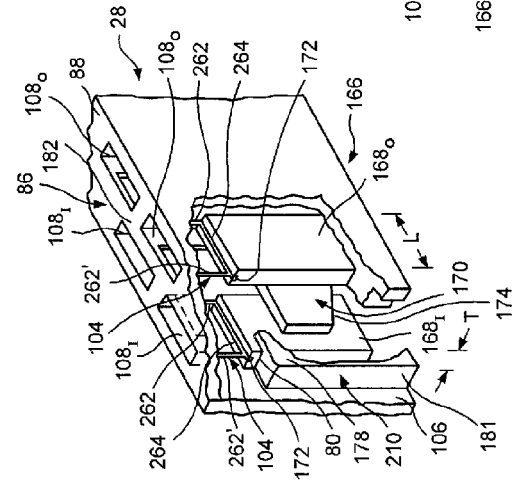

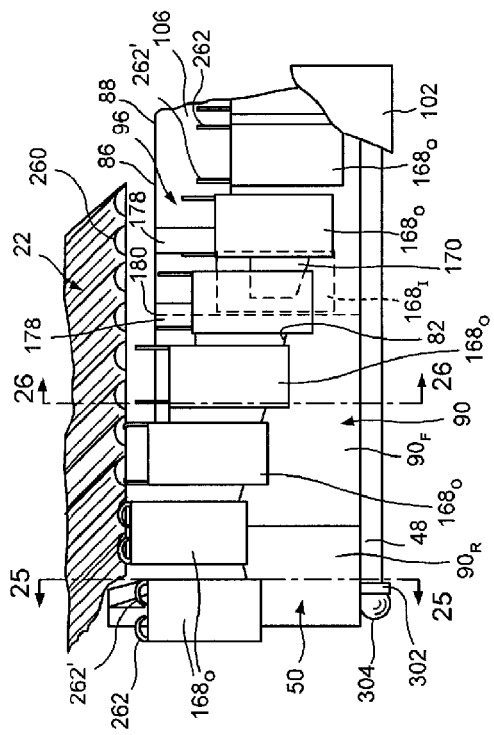
FIG. 24
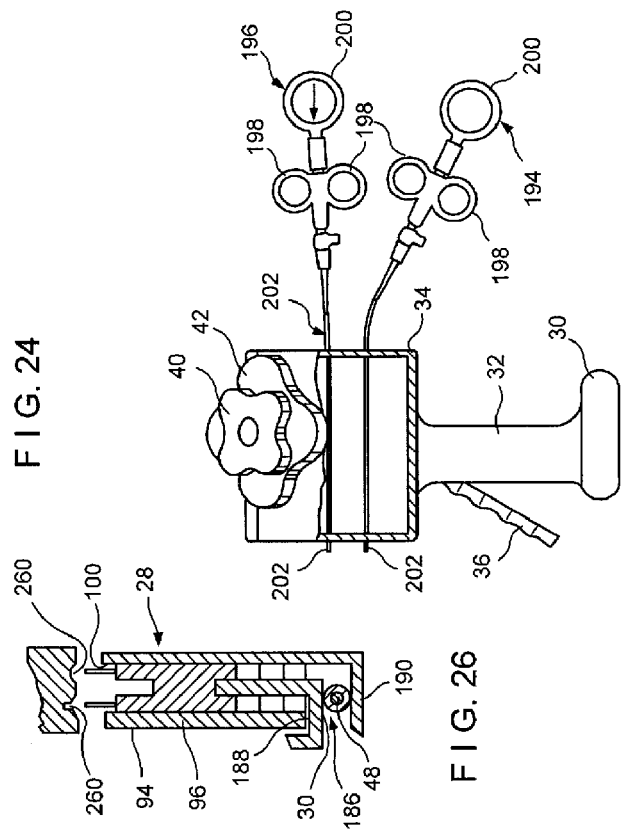
FIG. 26
FIG. 27

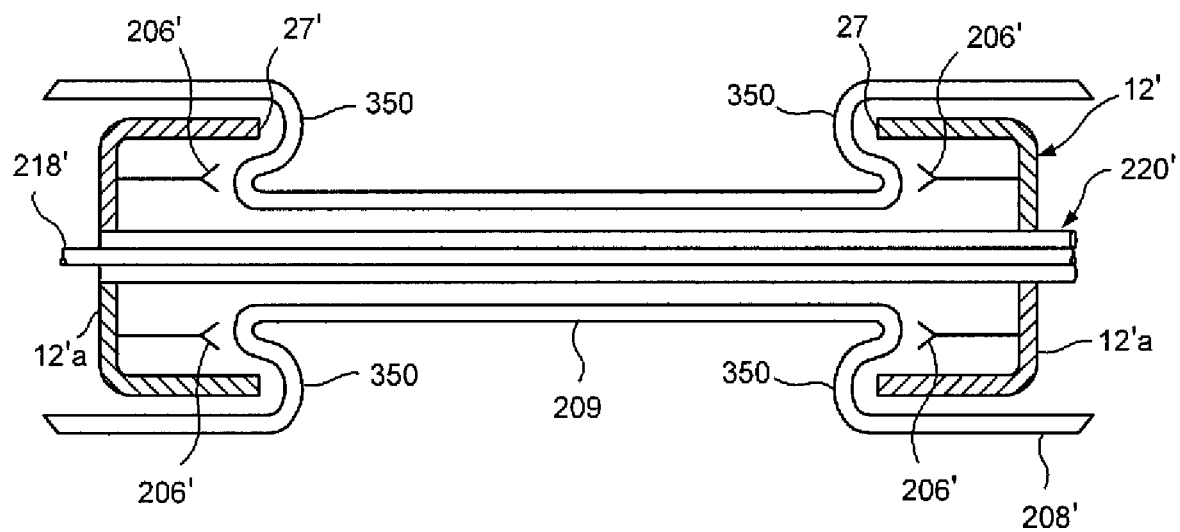
F I G. 32

SURGICAL APPARATUS AND METHOD

PRIORITY CLAIM

The present application is a Continuation application of U.S. patent application Ser. No. 09/697,306 filed on Oct. 27, 2000 now U.S. Pat. No. 7,235,089 Entitled "Surgical Apparatus and Method", which is a Continuation application of U.S. patent application Ser. No. 08/988,052 filed on Dec. 10, 1997 now U.S. Pat. No. 6,264,086 entitled "Surgical Apparatus and Method", which is a Continuation application of U.S. patent application Ser. No. 08/352,325 filed on Dec. 7, 1994 now U.S. Pat. No. 5,868,760 entitled "Method and Apparatus for Endolumenally Resectioning Tissue". The entire disclosure of these applications is expressly incorporated herein by reference.

FIELD OF THE INVENTION

This invention relates to surgical apparatus and procedures and specifically to surgical apparatus and procedures for resectioning, preferably endolumenally, diseased or otherwise undesirable portions of lumenal or other tissue and anastomizing remaining, healthy lumenal or other tissue.

Lexicon

This invention relates to surgical apparatus and procedures and accordingly, utilizes terminology from the medical and mechanical engineering fields. To facilitate understanding of this invention by workers in both fields, the following lexicon is provided; it is to be understood that plurals and close variants of these words also have the meanings indicated:

Anastomose: To connect or join by anastomosis; to communicate by anastomosis.
Anastomosis: The union of parts or branches (such as streams, blood vessels, or leaf veins) so as to intercommunicate; a product of anastomosizing, such as a network.
Anastomize: To cut in pieces in order to display or examine the structure and use of the parts; to dissect.
Appendicolith: A stone within the appendix.
Cannulation: Insertion within a lumen.
Endoscopy: Visual inspection of any cavity of the body by means of an endoscope.
Endolumenally: Pertaining to the intralumenal aspect of a hollow organ.
Enterotomy: Cutting completely through the bowel wall irrespective of the direction of cutting.
Laparotomy: Surgical incision through the flank to gain access to the peritoneal cavity.
Lesion: Any pathological or traumatic discontinuity of tissue or loss of function of a body part.
Ligate: To tie or band with a ligature in order to crush or strangulate.
Lumen: The cavity of a hollow organ.
Morbid: Of, relating to or characteristic of disease.
Mural: Pertaining or occurring in the wall of a cavity.
Polypectomy: Surgical removal of a polyp.
Resection: Surgical removal of part of an organ or structure.
Serosal: Pertaining to or composed of any serous membrane.
Sessile: Attached by a base; not pedunculated or stalked.
Staple: Tissue ligature or suture.
Submucosal: Pertaining to the submucosa; situated beneath the mucous membrane.
Transect: A section made across a long axis; a cross-section; division by cutting transversely.
Transmural: Through the wall of an organ, extending through or affecting the entire thickness of the wall of an organ or cavity.

DESCRIPTION OF THE PRIOR ART

Endoscopy studies the intra-lumenal aspects of hollow organs of the upper and lower intestine including the esophagus, stomach and the colon through cannulation of the lumen via the mouth or anus.

Endoscopic polypectomy is presently limited to a submucosal resection. The endoscopist is often unable to completely resect a sessile polyp or lesion and therefore the patient is subjected to subsequent definitive surgery, i.e. resection of the base of the tumor. Endoscopic polypectomy can be used to debunk sessile masses but it is unable to resect mural disease. Incomplete resection of a sessile polyp may destroy the biopsy specimen and alter the relationship of the gross specimen given to the pathologist thereby resulting in the pathologist possibly providing incorrect or incomplete study results. The endoscopist is also unable to correct uncommon but life threatening procedural complications such as perforations.

Surgical approaches for resectioning diseased tissue are largely practiced by making large laparotomy incisions or using minimally invasive techniques such as laparoscopic surgery in which tissues are resected and repaired through small incisions.

There are numerous surgical devices enabling surgeons to resect diseased tissue and subsequently anastomosize remaining tissue either through a conventional incision or using a laparoscope and making one or more relatively small incisions. Additionally, endoscopically assisted stapling devices are known which enable surgeons to remotely anastomose lumenal structures such as the bowel. Endoscopically assisted bowel anastomosis nevertheless typically requires extra-lumenal assistance via a traditional laparotomy incision or use of a laparoscope.

Trends in surgery are towards minimally invasive procedures as evidenced by developments including laparoscopic cholecystectomy, laparoscopic appendectomy and laparoscopically assisted partial colectomies and hernia repairs. All of these minimally invasive procedures involve introducing a laparoscope through the abdominal wall and creating other associated openings to gain access to the peritoneal cavity in order to perform the necessary surgical procedure. Typically, general anesthesia is required. Endoscopically possible procedures include polypectomy, mucosectomy, and cauterization.

Disadvantages of the laparoscopic method include the need to traverse the abdominal wall, increased operating time secondary to the lack of exposure for the procedure and possibly the need to convert to an "open" laparotomy in the course of performing the procedure.

Present stapling techniques in surgery are for the most part functionally adequate but limited. Devices exist including the GIA and EEA staplers which can be used to transect tissue in a linear and circular fashions respectively with subsequent anastomosis with staples. The linear GIA is relatively versatile. The EEA is primarily suited for lower colonic circular anastomosis after a lesion has been surgically removed (via laparotomy or laparoscopically) or during a colostomy takedown procedure.

The rigid post of the EFA stapler severely limits its use as well as requiring that an open procedure be utilized. The steerable endoscopic stapler is useful in allowing for more bowel accessibility; however, it remains dependent upon trans-abdominal surgical exposure prior to utilization.

While laparoscopic surgical instruments have been used for bowel anastomosis, in such procedures the bowel is anastomosized extracorporially or in an augmented stapled side-to-side fashion.

Possibly relevant to the patentability of this invention are U.S. Pat. Nos. 5,156,614; 5,170,925; 5,172,845; 5,180,092; 5,188,274; 5,188,638; 5,197,648; 5,197,649; 5,217,472; 5,219,111; 5,220,928; 5,221,036; and 5,242,457.

Non-patent prior art possibly relevant to the patentability of this invention includes the article "An Endoscopic Stapling Device: The Development of a New Flexible Endoscopically Controlled Device for Placing Multiple Transmural Staples in Gastrointestinal Tissue" appearing at pages 338 and 339 of Gastrointestinal Endoscopy, vol. 35, no. 4, published in 1989, and the article "An Endoscopic Sewing Machine" appearing at pages 36 through 38 of Gastrointestinal Endoscopy, vol. 32, no. 1, published in 1986.

OBJECTS OF THE INVENTION

An object of this invention is to provide methods and apparatus for performing transmural surgical procedures endolumenally without requiring incisions in the skin.

It is another object of this invention to provide methods and apparatus for endolumenal surgery resulting in decreased morbidity and mortality relating to or resulting from general anesthesia and further providing decreased post-operative recovery time secondarily to the lack of a body surface incision.

It is another object of this invention to provide methods and apparatus for improved treatment of lesions such as bowel tumors, providing the opportunity to diagnose, resect and cure patients without the need for subsequent open laparotomy or laparoscopic surgery.

It is another object of this invention to provide apparatus for endolumenal surgery where the apparatus is a coaxial unitary assembly.

It is another object of this invention to provide such apparatus which is flexible in order to reach any portion of the bowel or any other lumen into which the apparatus is inserted.

SUMMARY OF THE INVENTION

This invention facilitates preferably endoscopically or radiologically assisted, preferably visually guided endolumenal surgery to resect diseased tissue in a full transmural fashion. Once the resection has occurred, the invention facilitates anatomization of clean margins in either an end-to-end anastomosis or a simple enterotomy closure. The invention is not limited to any particular or specific direction, orientation or shape of the incision or performance of such incision in the course of resectioning; both radial and longitudinal incising are within the purview of the invention.

The apparatus and methods of the invention for endolumenal surgery may be used to perform multiple surgeries including but not limited to full-thickness transmural polypectomies, resections of submucosal lesions, bowel resections, resections of processes such as ulcers that have violated mucosa and deeper structures, and to control bleeding. The apparatus and methods may also be used to close perforations via transmural stapling. Many other endolumenal procedures may also be performed utilizing the invention including prophylactic or therapeutic appendectomies, resection of bleeding diverticuli or a Meckel's diverticulum, anchoring tubes or time-released medications, performing gastroplasty, fallopian tubal ligation, solid organ biopsies, bowel structuring or partial lung resectioning.

As a result of the flexible nature of the apparatus and methods of the invention, an operator with either endoscopic or diagnostic imaging guidance can use the apparatus to perform transmural surgery with resection and subsequent anastomosis non-invasively. The invention is not limited to use with endoscopic or a particular type of diagnostic imaging guidance; magnetic resonance imaging (MRI), CAT scans (CT), fluoroscopic imaging and ultra-sonic imaging guidance may all be used in connection with the apparatus of the invention and in connection with practice of the methods of the invention.

With the invention, decreased invasiveness lowers morbidity for the patient and allows for faster recovery with less time as a patient in the hospital. Laparoscopy coupled with endolumenal surgery greatly facilitates performance of additional surgical procedures and tissue biopsy.

In one of its aspects this invention provides apparatus for endolumenally resectioning a diseased portion of lumenal tissue in a manner that remaining lumenal tissues are anastomsed with fastening means. In such aspect the apparatus includes means for gripping histologically normal lumenal tissue, preferably at axially separated positions on respective sides of the diseased tissue of interest, and pulling the gripped tissue via mechanical compression with traction or via suction, i.e. negative pressure with traction, into a cutting zone removed from an undisturbed portion of the lumenal tissue. Since the diseased or other undesirable tissue of interest is surrounded by the gripped histologically normal tissue, the diseased or other undesirable tissue of interest is pulled into and preferably across the cutting zone.

The apparatus further preferably includes means for detaching the diseased lumenal tissue from surrounding healthy lumenal tissue and further fastening tissue together so that healthy lumenal tissue is fastened about and across an aperture in the lumenal wall, which aperture would otherwise be created by detachment of the diseased or otherwise undesirable lumenal tissue from the healthy lumenal tissue, in a manner to close the aperture. The tissue fastening and detaching means preferably operates to fasten the healthy tissue together before cutting the diseased or otherwise undesirable tissue therefrom in a manner minimizing chances for diseased tissue subsequently contacting healthy tissue and further minimizing likelihood of any aperture remaining for leakage of material through the tissue wall from which the diseased or undesired tissue was removed.

The tissue fastening means portion of the apparatus preferably may further include a plurality of suturing staples and anvils for the fastening, bending or closing of individual suturing staples serially there against.

Preferably in one embodiment of the apparatus aspect of the invention the cutting means portion of the apparatus includes a longitudinally elongated blade which preferably translates along a longitudinal axis respecting the remainder of the apparatus and respecting a lumen into which the apparatus has been inserted.

In the stapling and cutting aspect of the invention, the invention is not limited to a single length stapling and cutting operation. The stapling and cutting operation may be along only a limited portion of the stapling and cutting path so that if the objective of the surgery is removal of a polyp or perhaps the appendix, where the tissues to be removed are relatively small and/or encountered in a head-on orientation, the operating physician or other attending health professional may adjust and control the length of the path over which tissue stapling and cutting is performed.

The invention is not limited to combining tissue stapling and tissue cutting aspects together. The tissue stapling aspect of the invention may be practiced without the tissue cutting aspect of the invention and the apparatus may be configured to provide only tissue stapling or other types of tissue suturing or fastening, without tissue cutting being present. This facilitates use of the invention in surgical procedures where tissue fastening is required without or only ancillary to tissue cutting.

Further preferably in one embodiment of invention the fastening means portion of the apparatus includes means for advancing staples preferably serially against anvils.

In one of the apparatus aspects of the invention, there is provided a preferably longitudinally elongated operating capsule including an outer shell preferably having a curved end at one longitudinal extremity thereof with the outer shell preferably including an upper shell portion and a lower shell portion. Hinge means preferably connect the upper and lower shell portions and are generally longitudinally aligned and positioned along a longitudinally elongated portion of the shell to facilitate separation of the shell portions and opening of the shell by relative rotation of the shell portions about the hinge means. When the shell portions are closed, respective facing lip portions may be spaced one from another. The lip portions preferably define a tissue stapling and cutting path and preferably extend around a portion of the curved end of the shell and along the longitudinally elongated portion of the capsule, allowing for both radial and longitudinal resections.

The capsule preferably further includes anvil means preferably resident in at least one of the facing lip portions extending along the curved and longitudinally elongated parts thereof. Suturing staple means preferably are resident in the remaining lip portion and preferably extend along the curved and longitudinally elongated lip parts facing the anvil means. The suturing staple means pass through any tissue positioned between the respective lips (and hence positioned between the suturing staple means and the anvil means), with the preferably individual suturing staple means curling back, respecting the direction of suture staple initial movement, into tissue positioned between the respective lips of the upper and lower shell portions. The suturing staple means preferably curl away from the anvil means due to contact therewith, thereby securing the tissue together along a line between the suturing staple means and the anvil means.

The operating capsule further preferably includes gradational tissue suturing staple advancement and tissue cutting means movable along the lip portion having the suturing staples resident therewithin. The gradational suturing staple advancement and tissue cutting means preferably sequentially advances the staples serially against the anvil means in the opposing lip via a preferably transversely flexible ramp assembly when the capsule is closed and the shell portions are close together, thereby effectuating suturing staple securement of tissue between one shell lip housing the suturing staple means and a second shell lip housing the anvil means. The suturing staple advancement and tissue cutting means is characterized as "gradational" to denote the feature whereby tissue stapling and cutting may be performed along any selected length of tissue; there is no need to cut along the entire length of permissible travel of the suturing staple advancement and tissue cutting means.

The operating capsule further preferably includes a transition portion at one end of the shell, adjoining the upper and lower shell portions, for connecting the operating capsule to a preferably flexible tubular member carrying cable or other means for controlling operation of the capsule.

In another of its aspects the capsule preferably further includes means for opening the shell preferably by effectuating relative rotation of the shell upper portion with respect to the shell lower portion, which means preferably includes a threaded shaft rotatably mounted within the transition portion of the operating capsule and a carrier threadedly engaging the shaft and movable axially therealong responsively to shaft rotation. The carrier is preferably pivotally connected to one of the shell portions for pivotally moving the shell portions about the hinges upon movement of the carrier axially along the shaft.

The preferably intralumenal operation of the capsule facilitates passage of a conventional endoscope through the operating capsule in a manner that the endoscope may be considered to "snake" or "telescope" into and out of the capsule, moving preferably essentially coaxially with the capsule and the tubular connection member via which the capsule communicates with the operating control module. The endoscope allows the operator visually to guide the operating capsule up the lumen, with the endoscope preferably protruding from the end of the capsule via an aperture remote from the operating control module to provide excellent vision for the operator.

Once the operator, using the endoscope and the view afforded thereby, has guided the capsule up the lumen to the desired position, the endoscope may be withdrawn into the capsule to permit the operator to observe the tissue grasping, stapling and cutting operation performed by the operating capsule from within the capsule. After the diseased or otherwise undesirable tissue is cut and separated from surrounding healthy tissue, the capsule may be opened thereby permitting the operator to observe the wound and the stapling closure thereof with the endoscope and further to cauterize any bleeding blood vessels as needed. Even if there is no bleeding, the operating capsule may still be opened to allow inspection of the wound site using the endoscope in order that the operator may be sure there are no apertures or other sites where leakage could take place through healthy lumen wall tissue. Alternatively, the endoscope may be advanced axially out of the capsule, further up the lumen from the capsule, to observe the wound and the stapling closure thereof from outside the capsule.

In another of its aspects, the apparatus of the invention provides a flexible tubular member adapted for connecting an operating capsule to an operator control module where the flexible tubular member preferably includes an outer cylindrical sheath, an inner hollow cylindrical sheath concentric with the outer sheath and a plurality of preferably conical disks between the inner and outer sheaths. Desirably each disk has a hollow central preferably conical portion and an axial aperture preferably at the disk center, with the inner sheath residing within the aperture. Each disk further preferably includes an annular flange preferably at the base of the conical portion of the disk. A convex conical exterior surface of the conical portion of each disk preferably extends through the annular flange and preferably fits into the hollow central conical portion of an adjacent disk; this permits the disks to be in sliding complemental contact with each other. Each flange of each disk preferably has a plurality of slots extending radially inwardly from the flange periphery to accommodate control cables which extend through the flexible tubular member over the entire longitudinal length thereof.

In yet another of its aspects, the apparatus of the invention preferably includes an operator control module which preferably includes trigger means for pulling on a first cable and thereby drawing suturing staple advancing and tissue cutting means along a lip portion of the operating capsule shell having the suturing staples resident therewithin. The trigger means thereby serves to advance the staples preferably serially against anvil means in the opposing lip portion when the shell portions are closed and effectuates suturing staple securement of tissue positioned between the lip housing the suturing staple means and the lip housing the anvil means. The operating control module may further include helical spring means for biasing the trigger against movement in a direction to pull on the first cable.

The control module may further include a pair of pulleys mounted on shafts for unitary rotation therewith. In the apparatus aspect of the invention, a first cable preferably has its first end wrapped around a pulley within the control module rotated by the trigger, with a second end of the first cable connecting to the staple advancement and tissue cutting means in the operating capsule by travel through the cable carrying flexible tubular member. A second cable preferably wraps around a pulley within the control module associated with the knob means for moving the capsule left and right, extends from respective sides of such pulley through the cable carrying flexible tubular connection means and connects with a bulkhead portion of the capsule at respective positions which are left and right of the capsule vertical axis.

A third cable preferably wraps about another pulley within the control module which is associated with a knob for moving the capsule up and down, with the third cable extending from respective sides of such pulley through the flexible connection means and connecting with a bulkhead portion of the capsule at respective positions above and below a capsule horizontal axis.

A fourth cable preferably endlessly wraps around a pulley within the control module which is associated with the knob for opening and closing the capsule. The fourth cable preferably extends from respective sides of the pulley through the flexible connection means and connects with a pulley within the transition portion. The pulley within the transition portion preferably threadedly engages a stationary shaft extending generally perpendicularly to a plane defined by juncture of said upper and lower portions. The pulley within the transition portion preferably traverses the shaft due to relative rotation therebetween and is connected to the shell upper portion, to open and close the shell upper portion relative to the shell lower portion as the pulley moves respectively up and down the shaft due to rotation of the knob portion of the operator control module, for opening and closing the capsule.

In yet another apparatus aspect this invention provides apparatus for endoluminally removing a cylindrical wall section of undesired lumenal tissue and circumferentially securing remaining lumenal wall tissue from either side thereof annularly about the site of said cylindrical wall section removal. In this aspect the apparatus preferably includes means for fastening together circular margins of lumenal tissue which are adjacent to the undesired lumenal tissue which will be removed as a section of cylindrical lumenal tissue, to prevent creation of a cylindrical breach in the lumen which would otherwise result upon removal of the undesired lumenal tissue as a cylindrical section.

In this apparatus aspect the invention preferably yet further includes means for cutting the undesired lumenal tissue, as a cylindrical section from the lumen, radially inboard of the fastened together circular margins of the lumenal tissue. Preferably in this apparatus aspect of the invention the tissue fastening and cutting means fastens the tissue simultaneously around the entire 360° of the circular tissue margin. In this apparatus aspect of the invention the tissue fastening and cutting means preferably also cuts the tissue simultaneously around the entire 360° of the circular tissue margin. Further respecting this apparatus aspect of the invention, the tissue fastening and cutting means is preferably means for sequentially fastening and then cutting the tissue. In yet another aspect this embodiment of apparatus of the invention includes means for stapling tissue together as at least a part of the tissue fastening means.

In yet another aspect this invention provides apparatus for performing endolumenal tubular cylindrical resection where the apparatus includes a continuous annular lip. Suturing means are preferably present in the lip for passing through tissue positioned around the lip and thereby securing the tissue together. In this aspect of the apparatus of the invention the suture advancement and tissue cutting means is preferably moveable at the annular lip, for advancing the suturing means through the tissue thereby effectuating suturing securement of tissue simultaneously entirely around the annular lip and cutting the tissue inboard of the sutured securement simultaneously entirely around the annular lip.

In yet another aspect this invention provides methods for endolumenal full thickness resectioning of tissue by anastomizing the tissue with artificial fastening means.

One preferred practice of one of the method aspects of the invention includes inserting a tissue cutting instrument into a body lumen through a naturally occurring body orifice or a surgically created rent. A second step in the method is to advance the instrument within the lumen to an area of diseased tissue or tissues desired to be resected, where surgery is to be performed to remove the diseased tissue or to ligate a lumen. Yet another step of the method is to suture surrounding tissue defining a wall of the lumen to close an orifice therein which would otherwise result from removal of undesirable tissue urged or drawn or manipulated into position for cutting. Yet another step of the method is the cutting of the diseased urged or drawn or manipulated tissue from surrounding tissue defining a wall of the lumen in which the instrument resides.

An optional step is that of alternately urging or drawing or manipulating the tissue to be resected into an inner cavity of the instrument.

Another optional step is that of retaining the cut tissue, which has been urged or drawn or manipulated into the inner cavity of the instrument, in a position spaced or separated from the lumen wall. Yet another step is that of withdrawing the instrument along the lumen and from the body orifice while retaining the cut tissue, which had been urged or drawn or manipulated within the inner cavity of the instrument, in position spaced or separated from the lumen wall.

In still another aspect this invention provides a method for endolumenally cylindrically resectioning lumenal tissue where the method includes inserting a tissue and suturing cutting instrument into a body lumen through a naturally occurring body orifice. A second step in the method is to advance the instrument within the lumen to an area of undesired lumenal tissue to be cylindrically resectioned. A third step of the method is to draw the undesired lumenal tissue to be cylindrically resectioned into an annular cutting zone associated with the instrument. A fourth step in the method is that of stapling the surrounding lumenal tissue about annular margins of the cylindrical tissue to be resectioned to close an orifice which would otherwise result from removal of the undesired lumenal tissue as a cylindrical section of tissue. A fifth step in the method is that of cutting the undesired cylindrical lumenal tissue from surrounding lumenal tissue.

An optional step in the method is that of retaining the cut undesired cylindrical lumenal tissue within the instrument while withdrawing the instrument from the lumen through the naturally occurring orifice to maintain the cut undesired cylindrical lumenal tissue separated from healthy lumenal wall tissue.

In practice of this method aspect of the invention tissue stapling is preferably performed simultaneously around the entire 360° of the tissue circular margin. Similarly, the tissue cutting step is preferably performed simultaneously around the entire 360° of the circular tissue margin.

An important aspect of the methods and the embodiments of apparatus of the invention is that suturing the tissues surrounding diseased tissue, where the surrounding tissue defines a wall of the lumen, may be performed prior to cutting diseased or undesired tissue from surrounding tissue defining a wall of the lumen in which the apparatus of the invention resides.

An important optional aspect of the methods and apparatus of the invention is retention of the cut and removed tissue within the apparatus interior, away from the lumen wall. This is important in that it minimizes chances for contact of the severed diseased or otherwise undesired tissue with the healthy tissue remaining as a part of the body.

Another important aspect of the methods and apparatus of the invention is that whereby when malignant, diseased or otherwise undesirable tissue is to be removed from the lumen wall, the entire wall structure through its entire thickness is cut and removed; no layers of tissue are excluded or left in place. Further, the methods and apparatus of the invention facilitate complete removal of the wall tissue by reducing and effectively minimizing the opportunity for any diseased tissue to remain after resectioning has been completed.

The methods and apparatus are also applicable to procedures for healthy, normal tissue such as resectioning the Fallopian tubes for sterilization.

The invention also has applicability to performing appendectomies. In such case, the operator may use a balloon and a conventional endoscope together with apparatus of the invention to draw the appendix into the bowel interior and into an operating capsule portion of the apparatus of the invention without completely inverting the appendix. The appendix is desirably only partially inverted; however, complete inversion is also acceptable. Once the appendix has been sufficiently drawn into the operating capsule, the suturing and tissue cutting operation is performed at the base of the appendix with the appendix being retained within the operating capsule. This procedure is particularly desirable and indicated when an appendicolith has been detected.

The methods and apparatus, while directed principally to surgery of the gastrointestinal system, are also applicable to surgery for other organ systems including the genital-urinary tracts. The apparatus may also be used and the methods may be modified for use through small skin incisions so as to perform biopsies and to resect tissues remotely using endoscopic, radiological or other types of imaging as set forth above, within a body cavity such as the thoracic cavity or the abdominal cavity. Further, endovascular surgery may be performed using the apparatus and the methods of the invention.

BRIEF DESCRIPTION OF THE DRAWINGS

FIG. 1, which is divided into

FIG. 1A isometrically illustrates an operating control module portion of such apparatus embodying aspects of the invention and a part of cable carrying flexible tubular apparatus also manifesting aspects of the invention.

FIG. 1B isometrically illustrates a longitudinally elongated operating capsule apparatus manifesting aspects of the invention and the portion of the cable carrying flexible tubular apparatus not shown in FIG. 1A.

FIG. 2 is a side view of the apparatus illustrated in FIG. 1 with a conventional endoscope illustrated in position within the apparatus shown in FIG. 1, illustrating the manner in which an endoscope is used in conjunction with a preferred embodiment of apparatus manifesting aspects of the invention to remove malignant, other diseased or otherwise undesirable tissue from a lumen wall while within the lumen.

FIG. 3 is an enlarged broken view of a portion of the cable carrying flexible tubular apparatus manifesting aspects of the invention, taken as indicated by the box labeled "FIG. 3" in FIG. 2.

FIG. 4 is a sectional view of the cable carrying flexible tubular apparatus taken at lines and arrows 4-4 in FIG. 2.

FIG. 5 is a sectional view of the cable carrying flexible tubular apparatus taken at lines and arrows 5-5 in FIG. 4.

FIG. 6 is a side view of two conical disks, showing the disks in spaced relation, which reside within the cable carrying flexible tubular apparatus illustrated in FIGS. 1A, 1B, 2, 3, 4 and 5.

FIG. 7 is a broken, partially sectioned view of operating control module apparatus manifesting aspects of the invention taken at lines and arrows 7-7 in FIG. 2, illustrating knob and cable movement to effectuate lateral movement of the operating capsule apparatus relative to the longitudinal axis of the operating capsule.

FIGS. 8 and 9 are top views of operating capsule apparatus illustrating left and right movement of the operating capsule relative to the longitudinal axis of the operating capsule.

FIG. 10 is a sectional view of operating control module apparatus taken at lines and arrows 7-7 in FIG. 2, illustrating knob and cable movement to effectuate vertical movement of the operating capsule apparatus relative to the longitudinal axis of the capsule.

FIGS. 11 and 12 are side views of operating capsule apparatus illustrating vertical movement of the operating capsule relative to the longitudinal axis of the operating capsule.

FIG. 15 is partially sectioned side view of the operating capsule apparatus manifesting aspects of the invention with the operating capsule illustrated in an open position.

FIG. 16 is a partially sectioned broken view, taken looking from left to right in FIGS. 10 and 13, of operating control module apparatus manifesting aspects of the invention.

FIG. 17 is a view similar to FIG. 16 but showing certain parts of the operating control module in different positions.

FIG. 18 is an isometric partially broken view of the operating capsule apparatus manifesting aspects of the invention with the capsule shown open to reveal parts of the tissue stapling and cutting apparatus.

FIG. 19 is an isometric view of a lip portion of a lower shell of the operating capsule apparatus manifesting aspects of the invention and as shown in FIG. 18, further revealing parts of the tissue stapling and cutting apparatus.

FIG. 20 is a side elevation of a suture support member manifesting aspects of the invention.

FIG. 21 is a top view of the suture support member illustrated in FIG. 20.

FIG. 22 is a front view of the suture support member illustrated in FIGS. 20 and 21, taken looking from left to right in FIG. 20.

FIG. 23 is an isometric view of the suture support member illustrated in FIGS. 20, 21 and 22, showing the suture support member in place within the lower lip of the operating capsule.

FIG. 24 is a partially broken side elevation of the interior of a part of the lower lip portion of the operating capsule apparatus illustrated in FIG. 19.

FIG. 25 is a sectional view of the lower lip of the operating capsule illustrated in FIGS. 18, 19 and 24, taken at lines and arrows 25-25 in FIG. 24.

FIG. 26 is a sectional view of the lower lip of the operating capsule illustrated in FIGS. 18, 19 and 24, taken at lines and arrows 26-26 in FIG. 24.

FIG. 27 is a partially broken side elevation of operating control apparatus manifesting aspects of the invention, taken from the same side as FIGS. 16 and 17.

FIG. 32 is a schematic side elevation in section of a second embodiment of apparatus for removing malignant or other undesirable tissue from the wall of a lumen (such as the colon), while within the lumen (such as the colon), by removing a cylindrical segment of the lumenal wall which includes such malignant or other undesirable tissue, manifesting aspects of the invention.

Figure 1A:
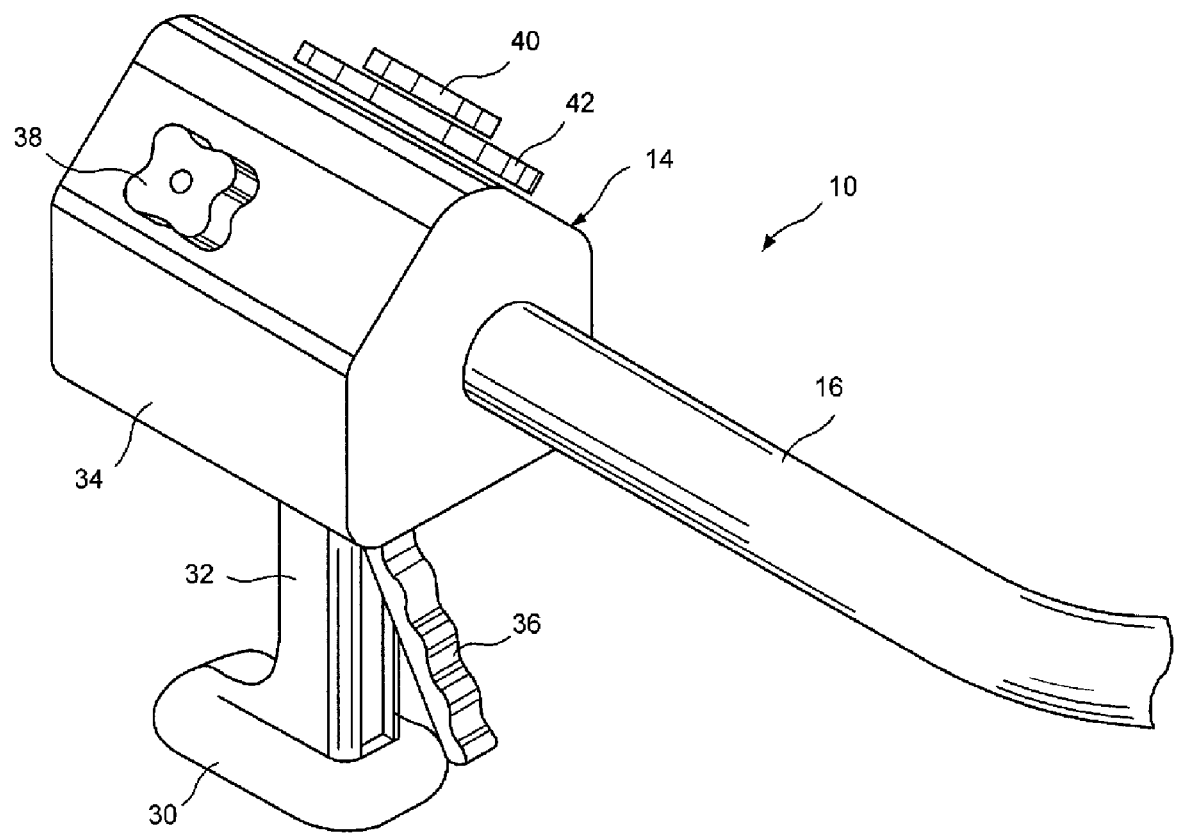
FIGS. 1A and 1B, is an isometric view of a first and preferred embodiment of apparatus for removing malignant or other undesirable tissue from the wall of a lumen (such as the colon), while within the lumen (such as the colon), manifesting aspects of the invention.

In the drawings and in the following text reference numerals used in the drawings identify correspondingly numbered structure described in the text.

DESCRIPTION OF THE PREFERRED EMBODIMENTS AND BEST MODE KNOWN FOR PRACTICING THE INVENTION

Figure 1B:
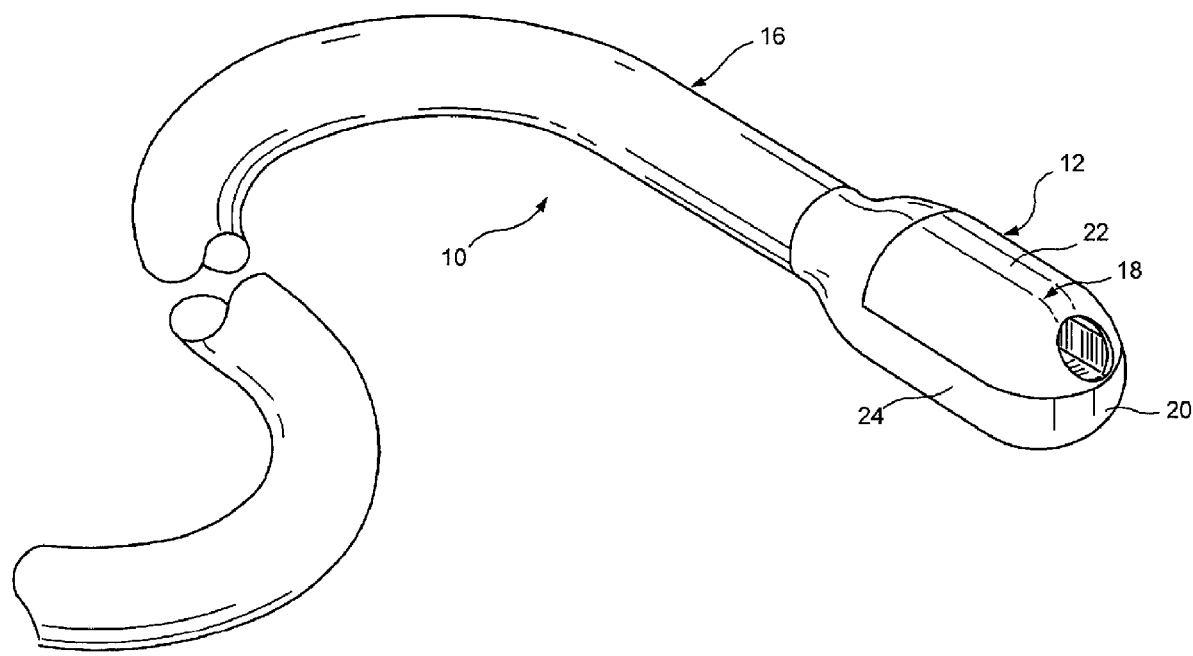

Referring to the drawings in general and to FIGS. 1A and 1B in particular, apparatus for removing malignant, other diseased or otherwise undesirable tissue from a lumen wall, such as the colon wall, while within a lumen, such as the colon, is designated generally 10 and includes a longitudinally elongated operating capsule designated generally 12, an operating control module designated generally 14 and a cable carrying flexible tubular member, designated generally 16, connecting operating capsule 12 and operator control module 14. Operating capsule 12 preferably includes an outer shell 18 having a preferably curved end 20 at one longitudinal extremity thereof which is also a longitudinal extremity of apparatus 10.

FIG. 2 illustrates the manner in which a preferred embodiment of the apparatus from removing malignant, other diseased or otherwise undesirable tissue from a lumen wall, which apparatus is designated generally 10 and is illustrated in FIGS. 1A and 1B, is preferably used in conjunction with an endoscope where the endoscope is designated generally 216 and has a tip extremity 218 at the end of a flexible tubular transmission means 220 which fits within and passes through a passageway extending axially the length of the longitudinally elongated operating capsule 12 and the cable carrying flexible tubular member 16 of apparatus 10.

Endoscope 216 further includes a control segment designated generally 222 which is generally conical in configuration, as illustrated in FIG. 2. Control segment 222 includes an eyepiece 224, an input light source 226, a motion control disk 228, a motion control knob 230, an access port 232 and a push button control 234.

Tip extremity 218 of flexible tubular transmission means 220 of endoscope 216 includes a light provided by fiberoptics extending through flexible tubular transmission means 220 and receiving light from input light source 226. Tip extremity 218 of flexible tubular transmission means 220 is maneuverable by the physician or other attending health care professional by rotation of motion control disk 228 and motion control knob 230 and by axial advancement of endoscope 216 and particularly flexible tubular transmission means 220 thereof. Motion control disk 228 has curved edge cut-out portions removed therefrom to facilitate gripping of disk 228 by the fingers.

A physician or other attending health care professional can inspection the colon by inserting tip extremity 218 into the colon through the rectum and thereafter guiding tip extremity 218 up the colon, as flexible tubular transmission means 220 is further inserted into the colon, by watching through eyepiece 224. Fiberoptics connect eyepiece 224 with tip extremity 218 thereby providing the physician or other attending health care professional with a view ahead as flexible tubular transmission means 220 of endoscope 216 is advanced along the tortuous path defined by the colon. Optionally, the endoscope may have the viewing fiberoptics connected to a television camera, instead of or in addition to eyepiece 224, thereby permitting the physician or other attending health care professional to view the interior of the colon (as seen from tip extremity 218) on a high resolution television screen.

Endoscope 216 may further optionally be equipped with small heaters at tip extremity 218 to perform cauterizing functions as desired. Additionally, the physician or other attending health care professional can utilize access port 232 to insert a catheter or other flexible probe to pass through the length of flexible tubular transmission means 220 and out of tip extremity 218, to perform desired surgical or pathological procedures.

Further referring to FIGS. 4 and 5, flexible tubular transmission means 220 of endoscope 216 is illustrated in transverse or axial section in FIG. 4. Endoscope 216 has four axial passageways within and extending through flexible tubular transmission means 220; the passageways have been numbered 236 with subscripts 1 through 4 identifying respective ones of the four passageways. Typically, one passageway 236 carries a fiberoptic strand providing light at tip extremity 218, a second passageway 236 would carry a fiberoptic strand for transmitting the image seen at tip 218 to eyepiece 224 and/or a suitable television display device, a third passageway 236 carries control cables or other control mechanisms actuated by motion control disk 228 and motion control knob 230 while a fourth passageway 236 may be empty, permitting the physician or other attending health care professional to use a variety of devices insertable into such fourth passageway via access port 232. The fiberoptics, control mechanisms and the light transmission means resident within passageways 236 have not been illustrated in the drawings to avoid drawing clutter.

Flexible tubular transmission means 220 is preferably a flexible foam like or other material, other than for the presence of passageways 236 is solid and is surrounded by a flexible rubber, vinyl or other flexible smooth material sheath so that flexible tubular transmission means 220 may be inserted into the colon via the rectum without damage to rectal tissues.

Flexible tubular transmission means 220 when in place within apparatus 10 is preferably but not necessarily coaxial and concentric with cable carrying flexible tubular member 16, as generally illustrated in FIGS. 4 and 5.

Referring still to FIG. 2 and additionally to FIGS. 8, 9, 11, 12, 14, 15, 18, 28 and 30, outer shell 18 of operating capsule 12 includes an upper shell portion 22 and a lower shell portion 24 which are connected by hinges or other suitable hinging means, which are not visible in FIG. 1 but are shown schematically in FIG. 15 and are there designated generally 44.

Upper and lower shell portions 22, 24 are longitudinally aligned and movable relative to one another about hinges 44 or other hinging means so that upper and lower shell portions 22, 24 can move, thereby to open shell 18, by relative rotation of upper and lower shell portions 22, 24 about hinges 44.

Figure 14:
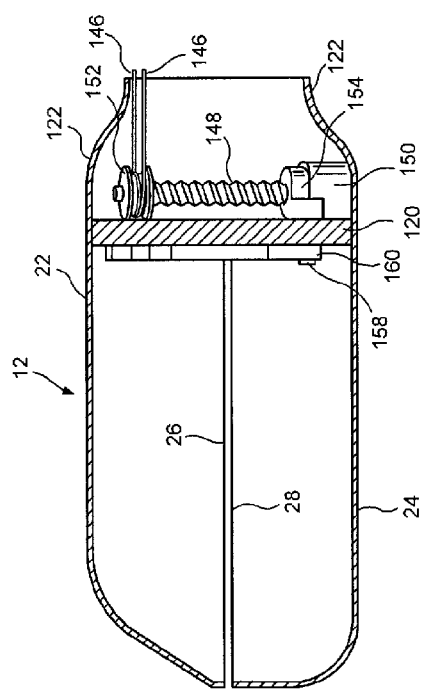
FIG. 14 is a vertical section, taken at lines and arrows 14-14 in FIG. 9, of operating capsule apparatus manifesting aspects of the invention with the operating capsule illustrated in its closed position.
Figure 28:
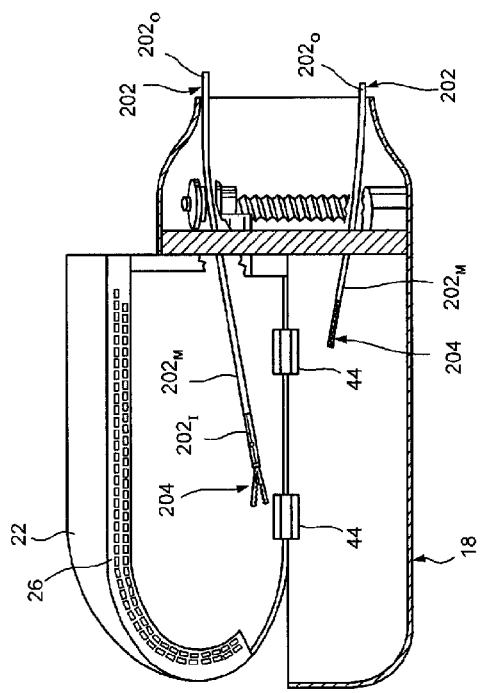
FIG. 28 is a side view of operating capsule apparatus manifesting aspects of the invention with the capsule shown open and with remotely actuable tissue grabbers illustrated within the operating capsule.

Upper and lower shell portions 22, 24 have respective lip portions 26, 28 which are preferably spaced from one another when outer shell 18 is closed and upper and lower shell portions 22, 24 are proximate one another, as shown in FIG. 14.

Referring to FIG. 1 and specifically to FIG. 1A and also to FIGS. 7, 10, 13, 16, 17, 27 and 29, operator control module 14 includes a base 30, a handle 32, a housing 34 supported above base 30 by handle 32, a trigger 36 and a plurality of control knobs, described in more detail below, facilitating remote operator control of operating capsule 12. These control knobs include an outer shell open/close control knob 38, an operating capsule left/right control knob 40 and an operating capsule up/down control knob 42, all illustrated in FIG. 1A. Control knobs 38, 40 and 42 are mounted on respective shafts, which are largely hidden and hence are not numbered in FIG. 1A, for rotation of respective pulleys to actuate cables wrapped thereabout within housing 34. Various ones of control knobs 38, 40 and 42 are also illustrated in one or more of drawing FIGS. 7, 10, 13, 16, 17, 27 and 29.

Apparatus 10 for removing malignant, other diseased or otherwise undesirable tissue from a lumen wall, such as the colon wall, while within a lumen such as the colon is designed so that operating capsule 12 may be inserted into the colon through the rectum while operating control module 14 remains outside the patient's body but is connected to operating capsule 12 remotely by cable carrying flexible tubular member 16.

As best shown in FIGS. 16 and 17, operating control module 14 further includes a helically coiling spring steel member 54 which biases pivotally movable trigger 36 against movement in the direction to pull on a first cable 48 which is connected to pulley 52 and wrap about pulley 52 upon rotation thereof. First cable 48 extends through cable carrying flexible tubular member 16 into operating capsule 12 to connect with a ramp-knife assembly 50, which performs tissue fastening staple advancement and tissue cutting. Ramp-knife assembly 50 is desirably unitary in that the assembly is fabricated from a plastic-metal assembly or from a single piece of metal or plastic. Ramp-knife assembly 50 is illustrated in FIGS. 17 and 18 and is pulled by cable 48 along a path defined by lip portion 28 of lower shell portion 24.

Referring specifically to FIGS. 16 and 17, trigger 36 is connected to pulley 52 via a piece of helically coiling spring steel 54 defining a helical leaf-like spring. When actuating the tissue fastening staple advancement and tissue cutting means, specifically ramp-knife assembly 50, the operator pulls on trigger 36, pivotally moving trigger 36 about a pivotal mounting point 37 from the position illustrated in FIG. 16 towards the position illustrated in FIG. 17. As the operator pulls on trigger 36, helical coiling spring steel member 54 extends and a portion of helical coiling spring steel member 54 is pulled from a position of rest, where it is wrapped about a cylindrical shoulder portion 58 of pulley 52, thereby rotating pulley 52 in the direction illustrated by arrow A in FIG. 17. This action draws first cable 48 in the direction illustrated by indicator arrow $A_1$ in FIG. 17.

Drawing first cable 48 in this direction causes the remaining end of cable 48, which is connected to ramp-knife assembly 50 within operating capsule 12 as illustrated in FIG. 24, to pull ramp-knife assembly 50 along and within lip portion 28 of lower shell portion 24. If the operator pulls trigger 36 through the maximum angular range of travel for trigger 36, from the position illustrated in FIG. 16 completely to the position illustrated in FIG. 17, ramp-knife assembly 50 moves from the position illustrated in FIG. 18, along the entire curved and then straight length of lip portion 28, to the position illustrated in FIG. 19. Travel of ramp-knife assembly 50 is limited by contact of the leading edge of ramp-knife assembly 50, which leading edge is designated 300 in the drawings, with an upstanding portion of lower lip 28, as illustrated in FIG. 19. Hence, once the operator has pulled trigger 36 through its maximum angular range of travel, the operator will sense by finger feel that trigger 36 cannot be further pulled due to the contact of the leading edge of the knife-ramp assembly with upstanding support member 300 illustrated in FIG. 19.

It is not necessary that trigger 36 always be moved by the operator through its entire range of angular and linear travel to thereby pull ramp-knife assembly along the entire range of travel along lip 28. The physician or other attending health professional controlling trigger 36 may choose to advance ramp-knife assembly only along the curved portion of lip 28 illustrated in FIGS. 17 and 18. For example, the invention may be used to remove tissue encountered by the operating capsule in a head-on fashion, when moving in the direction indicated by arrow B in FIG. 18. Alternatively, if a large mass of tissue is to be removed, where the tissue drawn into operating capsule 12 overlies the entirety of lip portion 28, the physician or other attending health professional pulls trigger 36 through its full range of angular motion thereby to staple and cut tissue along the entire length of lip portion 28.

As illustrated in FIGS. 16, 17, 18 and 30, first cable 48 is preferably of the type including an inner strand housed within an outer sheath where the inner strand is preferably solid. Whether the inner strand is solid or braided, the inner strand is a high tensile strength material and is moveable axially respecting the outer sheath. The inner strand of first cable 48 is denoted 48, in the drawings while the outer sheath of first cable 48 is denoted 480. Inner strand 48, and outer sheath 480 have not been separately numbered in all of the drawings to avoid excessive drawing clutter.

Referring to FIGS. 3, 4, 5 and 6, cable carrying flexible tubular member 16, through which first cable 48 connects trigger 36 with ramp-knife assembly 50, includes an outer preferably cylindrical sheath 60, a hollow inner preferably cylindrical sheath 62, which is preferably but not necessarily concentric with outer sheath 60, and a plurality of preferably truncated or frusto-conical disks between outer sheath 60 and inner sheath 62. The individual conical disks are designated generally 64 in the drawings. Disks 64 are best illustrated in FIGS. 3, 4, 5 and 6.

Each individual conical disk 64 preferably includes a hollow central conical portion 66 and an annular flange 68 at the base of conical portion 66. Each disk 64 has an axial inner aperture 74 preferably at the center of conical portion 66 of the disk. Inner sheath 62 resides within axial inner apertures 74 of disks 64.

Each disk 64 preferably further has a convex conical exterior surface 70 formed on central conical portion 66. Each disk 64 also preferably includes a preferably concave conical surface 72 formed on the interior of central conical portion 66 and a preferably convex conical surface 70 formed on the exterior of central conical portion 66. Concave conical interior surface 72 is shaped for sliding, substantially complementally facing contact with convex conical exterior surface 70 of an axially immediately adjacent disk 64. This arrangement, facilitating movable, sliding and twisting contact between axially adjacent disks 64, is best illustrated in FIGS. 5 and 6.

The generally conical geometry of the portions of disks 64 extending from annular flanges 68 serves to maintain adjacent disks generally in coaxial and aligned position but nevertheless permits the column of disks 64 residing within outer cylindrical sheath 60 of flexible member 16 to twist and turn, in order to follow what may be a very tortuous path defined by a body lumen as operating capsule 12 travels axially within that lumen. The arrangement of the concave conical interior surface 72, in substantially complementally facing contact with convex conical exterior surface 70 of the immediately adjacent disk, provides sufficient rigidity that flexible member 16 cannot be sharply bent. This is important in order that flexible member 16 may keep cables, such as first cable 48 via which the operator at control module 14 controls operating capsule 12, from bending. If those cables bend and develop kinks, control over operating capsule 12 may be lost. Loss of control over operating capsule 12 could be catastrophic, requiring withdrawal of the apparatus 10 from the patient prior to completion of the surgical procedure of interest.

When cable carrying flexible tubular member 16 is bent to an extreme, interference between flanges 68 of adjacent disks 64 prevents further bending of tubular member 16 thereby minimizing the likelihood of any twisting of the control cables carried by and passing through cable carrying flexible tubular member 16.

The arrangement of disks 64 prevents self-collapse of cable carrying flexible tubular member 16 and also prevents telescoping of flexible tubular member 16. Disks 64 permit flexible tubular member 16 to transmit axial driving force, which is required to be applied by the physician or attending health care professional, to move operating capsule 12 and cable carrying flexible tubular member 16 axially along the colon.

Disks 64 facilitate transmission of that driving force axially even though the axis of the colon, and therefore the path being followed by operating capsule 12 and cable carrying flexible tubular member 16, is curvilinear. As cable carrying flexible tubular member is used to advance operating capsule 12 along the axis of the colon, the axis orientation is continuously changing as is the position or positions of curvature of flexible tubular member 16 as operating capsule 12 is inserted further and further into the colon. The arrangement of conical disks 64 within member 16 provides the requisite ability to axially transmit the necessary driving force as flexible tubular member 16 changes in position and orientation while advancing along the colon axis.

Referring to FIGS. 1A, 7, 8 and 9, left and right control of operating capsule 12 is effectuated by rotation of capsule left/right control knob 40. Capsule left/right control knob 40 is rotatably mounted on a shaft 112, which in turn is rotatably mounted in housing 34 of operating control module 14 and has a pulley 114 fixedly connected thereto as illustrated in FIG. 7. A cable 116, referred to as a "second" cable to distinguish cable 116 from "first" cable 48, is wrapped about pulley 114; respective ends of second cable 116 extend from operating control module 14 through cable carrying flexible tubular member 16 to operating capsule 12. Rotation of left/right control knob 40 in respective directions results in operating capsule 12 moving to the right and to the left relative to the longitudinal axis thereof as illustrated respectively in FIGS. 8 and 9. In FIGS. 8 and 9 the referenced longitudinal axis is denoted by hash marks and movement of operating capsule 12 to the right and to the left with respect thereto is denoted by arrows R and L in FIGS. 8 and 9 respectively.

Referring to FIG. 15, operating capsule 12 has an openable portion, defined by upper shell portion 22 and lower shell portion 24, and a transition portion denoted generally 118. Transition portion 118 is not openable; transition portion 118 serves to reduce the cross-sectional size of apparatus 10 from the cross-sectional size of operating capsule 12 in the area of upper and lower shell portions 22, 24 down to a smaller cross-sectional area as defined by the cross-section of cable carrying flexible tubular member 16.

Transition portion 118 includes a bulkhead 120 and an outer skin or shell portion 122 which is generally hollow as illustrated in FIG. 15.

Figure 30:
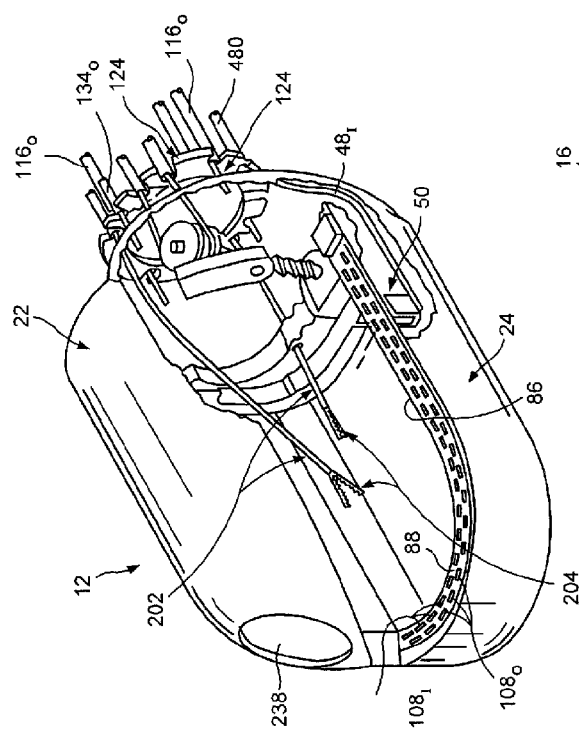
FIG. 30 is an isometric partially broken view of the operating capsule apparatus illustrated in FIGS. 1B, 2, 8, 9, 11, 12, 14, 15, 18 and 28, illustrating the tissue grabbers and control cables used to effectuate various motions and functions of the operating capsule.

Bulkhead 120 preferably provides a solid support and mounting area for the mechanism used to move upper shell portion 22 of capsule 12 as upper shell portion 22 is rotated relative to lower shell portion 24 thereby to open operating capsule 12. Additionally, bulkhead 120 provides support for removable lower lip portion 28. Furthermore, bulkhead 120 receives respective ends of second cable 116, specifically respective ends of inner strand $116_I$ of second cable 116. These respective ends of second cable 116 are preferably connected to bulkhead 120 at the lateral extremities of bulkhead 120 at a position on the vertical midpoint of bulkhead 120. Second cables 116 preferably enter transition portion 118 through respective appropriate slots in a flange 124 located at the axially opposite end of transition portion 118 from bulkhead 120. Flange 124 is illustrated in FIG. 30.

Respective outer strands $116_O$ of second cable 116 preferably reside within respective slots formed in flange 124 on diametrically opposite sides of flange 124, at the horizontal axis thereof. These respective ends of outer strands $116_O$ of second cable 116 are illustrated in FIG. 30. The tie-ins of inner strands $116_I$ to bulkhead 120 have not been illustrated in the drawings to avoid drawing clutter.

Respective ends of second cable 116 passing through cable carrying flexible tubular member 16 reside within diametrically opposed respective slots designated 126, 126' in annular flanges 68 of disks 64 as illustrated in FIG. 4. Second cable 116 enters cable carrying flexible tubular member 16 from housing 34 of control module 14 via a flange 128, illustrated in FIG. 7, which corresponds generally to flange 124 located at the opposite end of cable carrying flexible tubular member 16 and illustrated in FIGS. 17 and 24.

Referring generally to FIGS. 10, 11 and 12, up/down control of operating capsule 12 is effectuated generally by rotation of capsule up/down control knob 42 forming a part of operating control module 14. Capsule up/down control knob 42 is rotatably mounted on a shaft 130 which is rotatably mounted for rotation relative to and within housing 34 of control module 14. Fixedly connected to shaft 130 is a pulley 132 about which is wrapped a third cable 134. Similar to first and second cables 48, 116, third cable 134 desirably has a solid inner strand denoted with the subscript "I" and an outer sheath denoted with the subscript "O".

Respective portions of third cable 134 extend through cable carrying flexible tubular member 16 and into transition portion 118 where respective ends of third cable 134, specifically respective ends of inner strand $134_I$, are fixedly connected to bulkhead 120. These respective ends of third cable 134 are fixedly connected to bulkhead 120 at the top and bottom extremities of a vertical axis of operating capsule 12. These connections are not illustrated in the drawings to avoid drawing clutter.

Figure 29:
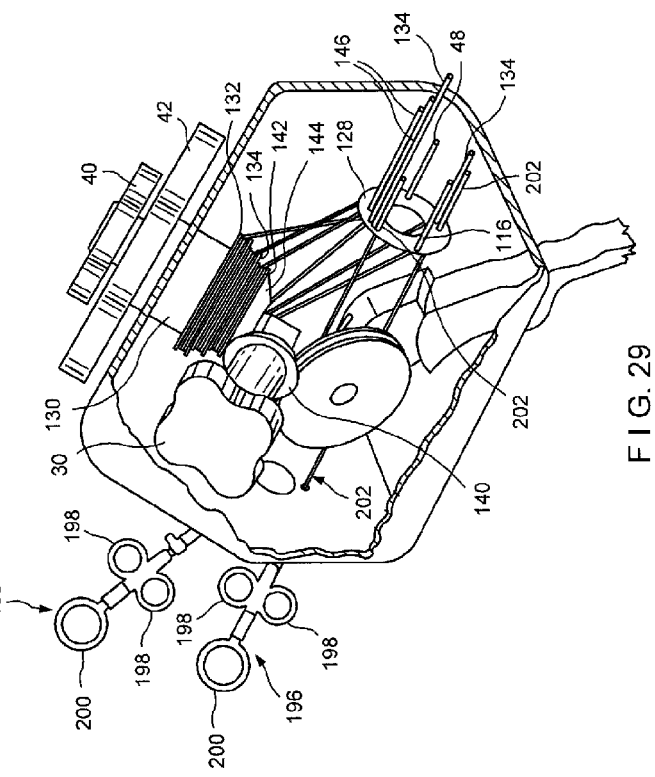
FIG. 29 is a partially broken isometric view of operating control module apparatus manifesting aspects of the invention illustrating control of certain portions of the operating capsule using control knobs of the operating control module.

Similarly to second cable 116 and first cable 48, third cable 134 enters cable carrying flexible tubular member 16 by passing through respective apertures in flange 128 and resides within slots 136, 136' in flanges 68 of disks 64, as third cable 134 extends the length of cable carrying flexible tubular member 16. This arrangement of third cable 134 passing through apertures in flange 128 is illustrated in FIG. 29. The arrangement of third cable 134 in slots 136, 136' in flanges 68 of disks 64 is illustrated in FIG. 4. The arrangement of third cable 134 in respective slots in flange 124, where third cable 134 enters transition portion 118, is illustrated in FIG. 30.

Rotation of capsule up/down control knob 42 in respective directions denoted by respective unnumbered arrows in FIG. 10 results in movement of operating capsule 12 up and down with respect to a longitudinal reference axis, as illustrated by arrows U and D in FIGS. 10 and 11 respectively, as cable 134 pulls in respective directions on bulkhead 120 due to rotation of pulley 132.

Capsule left/right control knob 40 and its associated pulley shaft and cable have not been numbered in FIG. 10 to avoid drawing clutter. Similarly, operating capsule up/down control knob 42, shaft 130, and pulley 132 and associated third cable 134 have not been illustrated in FIG. 7 to avoid drawing clutter.

Figure 13:
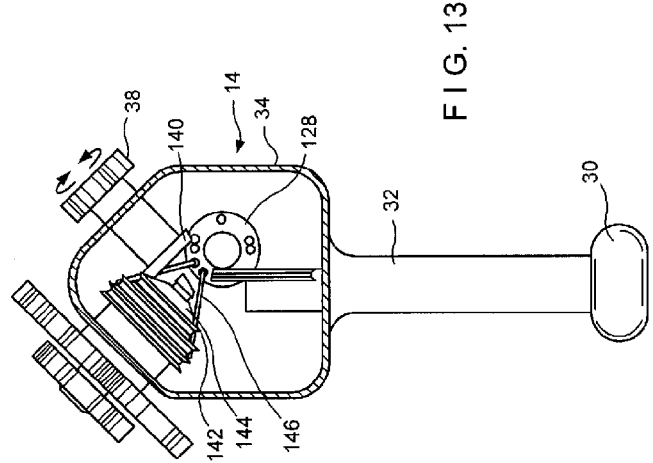
FIG. 13 is a sectional view of operating control module apparatus taken at lines and arrows 7-7 in FIG. 2, illustrating knob and cable movement to effectuate opening and closing of the operating capsule.

Referring to FIG. 13, opening and closing of operating capsule 12 is preferably effectuated by rotation of capsule open/close control knob 38 by the operator. Capsule open/close control knob 38 is mounted on a shaft 138 which is rotatably journaled within and extends into the interior of housing 34. A bevel gear 140 is fixedly mounted on shaft 138 at the end thereof opposite from capsule open/close control knob 38 within housing 34.

A pulley 142 is mounted coaxially with pulleys 114 and 132 but is freely rotatable independently thereof. Pulley 142 has a bevel gear surface 144 formed on one side thereof. The teeth of bevel gear surface 144 mesh with the teeth of bevel gear 140. Accordingly, rotation of capsule open/close control knob 38 and consequent rotation of bevel gear 140 serves to rotatably drive pulley 142 about its axis of rotation. A fourth cable 146 is wrapped about pulley 142 so that upon rotation of pulley 142, one of the two portions of fourth cable 146 extending therefrom is advanced off of pulley 142 while the remaining portion of fourth cable 146 is retracted by being wound onto pulley 142.

Fourth cable 146 extends from operating control module 14 through cable carrying flexible tubular member 16 and into transition portion 118.

Referring to FIGS. 13 and 14, a threaded shaft 148 is preferably rotatably mounted on a pedestal block 150 which is fixedly connected to bulkhead 120. A drive pulley 152 is fixedly mounted at one end of threaded rotatable shaft 148 and is rotatable unitarily therewith. Fourth cable 146 is preferably wrapped about drive pulley 152 as illustrated in FIGS. 13 and 14.

Advancement of one portion of fourth cable 146 and concomitant retraction of the remaining portion of fourth cable 146 due to rotation of pulley 142 responsively to rotation of capsule open/close control knob 38 causes rotation of threaded rotatable shaft 148.

A nut 154 threadedly engages shaft 148 and is movable freely therealong in response to rotation of shaft 148. Fixedly connected to nut 154 is an arm 156. Arm 156 extends generally horizontally from nut 154, towards the side of operating capsule 12 where lip portions 26, 28 are located; this is the side of operating capsule 12 which opens upon rotation of upper shell portion 22 relative to lower shell portion 24.

A pin 158 preferably extends generally longitudinally parallel with the axis of operating capsule 12 and cable carrying flexible tubular member 16, from arm 156 towards the curved axial and longitudinal extremity of operating capsule 12. Pin 158 has a shaft portion and a head portion, neither of which are numbered in the drawings. The head portion of pin 158 is mounted in a lift arm 160 connected to upper shell 22 and forming a portion thereof. Pin 158 passes through a slot or other opening in bulkhead 120 to provide the connection between arm 156 and lift arm 160.

As drive pulley 152 rotates threaded shaft 148 in a given direction, since shaft 148 is axially immovable nut 154 rides up or down shaft 148, depending on the direction of rotation of shaft 148. As nut 154 rides up shaft 148 when the apparatus is positioned as illustrated in the drawings, such rotation of shaft 148 causes upper shell portion 22 to rotate upwardly relative to lower shell portion 24 thereby opening operating capsule 12 as illustrated generally FIG. 18. Rotation of threaded shaft 148 in the opposite direction due to advancement of the remaining portion of fourth cable 146, causes nut 154 to ride downwardly along threaded rotatable shaft 148, causing upper shell portion 22 to rotate towards lower shell portion 24 thereby closing operating capsule 12 in response to rotation of capsule open/close control knob 38.

While the operating capsule open/close mechanism has been illustrated utilizing motion of a nut along a threaded shaft to effectuate the opening and closing, it is within the purview of the invention to provide one or more small electric or hydraulic motors to perform the opening and closing function. When such motors are used, gears or pistons on any other appropriate drive mechanism on means may be used to open and close the operating capsule.

Referring generally to FIGS. 18, 19, 24 and 26, ramp-knife assembly 50 is fabricated with a knife portion 76 having an inclined, leading tissue cutting edge 78. Ramp-knife assembly 50 further includes a horizontal base portion 80 and an inclined staple advancing ramp portion 82. First cable 48 is removably affixed to ramp-knife assembly 50, preferably to the bottom surface of horizontal base portion 80 at a position thereon immediately underneath inclined leading tissue cutting edge 78 of knife portion 76, as illustrated in FIGS. 18 and 24 through 26.

First cable 48 is preferably retained in position and removably affixed to ramp-knife assembly 50 by a spring-clip 302 which is affixed to the lower surface of ramp-knife assembly 50 as best illustrated in FIGS. 25 and 26. Spring-clip 302 retains an end of first cable 48 in engagement therewith; first end of cable 48 preferably is equipped with a knob 304, illustrated in FIG. 24, which interacts with spring-clip 302 so that when first cable 48 is advanced in a direction to the right in FIG. 24, interaction between spring-clip 302 and knob 304 forces ramp-knife assembly 50 to the right in FIG. 24. This arrangement with spring-clip 302 holding first cable 48 in place permits reuse of cable 48 and the major portion of capsule 12 once a suturing or stapling function has been performed and the staples have been used to secure tissue together and are no longer resident within lower lip 28 of capsule 12.

Preferably lower shell portion 24 of operating capsule 12 is fabricated of plastic, metal or some other suitably rigid material so that lower shell portion 24 has a hollow interior. Most preferably, lower shell portion 24 of operating capsule 12 is plastic, as is lip portion 28. This hollow interior, which is visible via the cut-aways in FIGS. 18 and 19 and in the sectional views of FIGS. 25 and 26, defines the curved and then straight path traveled by ramp-knife assembly 50 as ramp-knife assembly 50 is advanced and performs its staple advancing (for tissue fastening) and tissue cutting functions.

Most preferably lip portion 28 of lower shell 24 is constructed to be easily snapped into place and removed from the remainder of lower shell portion 24, with lip portion 28 preferably being constructed as illustrated in FIG. 19. Suitable snap-in and snap-out fixtures and geometry may be provided at respective ends of lip portion 28; one such snap-in and snap-out structure is denoted 84 in FIG. 19. The snap-in and snap-out construction of lip portion 28 is preferred in order that once staples have been placed into tissue and a given surgical procedure has been completed, a spent lip portion 28 may be removed from lower shell 24 and replaced with a fresh lip portion 28 loaded with suitable staples in order that operating capsule 12 may be reused numerous times to minimize costs associated with performance of such surgical procedures.

Respecting materials for operating capsule 12, so long as the materials may be adequately sterilized for reuse of operating capsule 12, any suitable plastic, metal or other suitable rigid or semi-rigid material or materials may be used. Use of plastic is preferred to provide compatibility with MRI.

Lip 28 has a longitudinally extending slot running along the lower inside portion thereof. Due to the positioning of lip 28 in FIG. 19, that slot cannot be seen in FIG. 19 but is clearly shown in the sectional views of FIG. 26. The slot, which is designated generally by indicator number 186 in FIG. 26, is defined by a lower extremity 188 of an inner wall 96 of lower lip 28 and a horizontal bottom surface 190 of lower lip 28.

An inner lateral extremity of horizontal base portion 80 of ramp-knife assembly 50, which supports an upstanding knife support 192 for knife portion 76 of ramp-knife assembly 50, extends laterally outwardly through and from that slot, inwardly into the interior of the capsule. This construction is illustrated in FIGS. 25 and 26.

Additionally, knife support 192, knife portion 76 and specifically leading knife cutting edge 78, extend above the upper extremity of lip assembly 28; the upper extremity is denoted 86 in FIGS. 19 and 25. Upper extremity 86 is defined by a preferably planar surface 88, best illustrated in FIG. 23, which may be horizontal or may be slightly inwardly inclined from the outer portion of lip 28 to the inner portion.

In either case, inclined leading knife cutting edge 78 of knife portion 76 extends above the upper inner edge of lip 28 defined by upper extremity 86. Hence, any tissue extending across planar upper surface 88 past edge 86 and into the interior of capsule 12 is cut by inclined leading tissue cutting edge 78 of knife 76 as ramp-knife assembly 50 traverses the curved and then straight path defined by the hollow interior of lower lip 28.

While the apparatus in the preferred embodiment has been illustrated with the opening between upper and lower lips 26, 28 of capsule 12 being generally at the horizontal mid-point of capsule 12, this is not required. The position at which upper lower shell portions 22, 24 of capsule 12 separate to provide the two facing lips where the tissue suturing and cutting function is performed does not have to be at the horizontal mid-point of capsule 12 and, indeed, does not even have to be a symmetrical position of closure respecting the longitudinal axis of capsule 12.

The preferred configuration of ramp-knife assembly 50 illustrated in FIGS. 18 and 19 and shown in section in FIGS. 25 and 26 lends stability to the assembly. Specifically, working surfaces of ramp-knife assembly 50 are desirably at least generally planar; exemplary of these are outboard surface 90 of suture advancing ramp, the bottom surface of ramp-knife assembly 50, namely the downwardly facing surface of horizontal portion 80 of ramp-knife assembly 50 which is not numbered in FIG. 19, 25 or 26, the exterior surfaces of knife support portion 192 and outboard (with respect to operating capsule 12 as a whole) surface 92 of knife portion 76 of ramp-knife assembly 50. Outboard surface 92 preferably rides in complementary facing contact with an inwardly (with respect to operating capsule 12 considered as a whole) facing surface 94 of inner wall portion 96 of lower lip 28, as illustrated in FIG. 19.

Ramp-knife assembly 50 may be fabricated with two separate portions of outboard or outwardly facing surface 90, a forward portion $90_F$ and a rearward portion $90_R$, where surfaces $90_F$ and $90_R$ may be at slight angles to one another about a vertical boundary therebetween denoted 98 in FIG. 19. This geometry may be desirable if the longitudinal length of ramp-knife assembly 50, denoted $L_I$ in FIG. 19, is relatively large with respect to the radius of curvature of the curved end of lower lip 28 and hence the radius of the resultantly curved portion of the path along which ramp-knife assembly 50 travels as it performs is tissue fastening staple advancement and tissue cutting function. That path is preferably defined by the hollow interior of lower lip 28.

In the preferred embodiment of the apparatus of the invention, ramp-knife assembly 50 is preferably fabricated of a single piece of flexible material, preferably plastic, with the material being flexible enough to permit the ramp-knife assembly to slide easily around the curved portion of the path along which ramp-knife assembly travels as it performs its tissue fastening staple advancement and tissue cutting function. Of course, the knife portion is preferably metal to provide an extremely sharp edge so that the tissue cutting results in a clean well defined cut.

Sliding, substantially complementally facing contact between surfaces $90_F$ and $90_R$ and the inwardly facing surface 100 of outer wall 102 of lower lip 28, as illustrated in FIG. 26, provides further stability as ramp-knife assembly travels within lower lip 28.

The tissue fastening staple apparatus aspects of the invention are best illustrated in FIGS. 18 through 26. Specifically referring to FIG. 20, individual staples 104 are preferably formed of extremely fine solid stainless steel wire, titanium wire or other suitable permanent or dissolvable tissue fastening stapling/suturing material. Each staple 104 is preferably initially formed of three straight portions, specifically two stapling fingers denoted 262 and 262' connected by a stapling base designated 264. Stapling fingers 262, 262' are preferably initially parallel to one another and preferably are of the same length. Stapling fingers 262, 262' extend from stapling base 264 preferably at substantially right angles to stapling base 264. Each staple 104 is preferably mounted in a respective staple support block of a staple support member.

Referring generally to FIGS. 20 through 23, a staple support member is designated generally 166 and includes two staple support blocks, which are designated 168, 168' respectively, connected integrally together by a generally trapezoidally configured solid adjoining member 170. Preferably, each staple support member 166 is of integral construction such that respective staple support blocks 168, 168' and adjoining member 170 are a unitary piece of preferably injection molded or compression molded plastic.

As apparent from FIGS. 20 through 23, staple support blocks 168, 168' of each staple support member 166 are preferably of rectangular solid configuration and are longitudinally offset one from another, as illustrated. Each staple support block 168, 168' preferably has a longitudinal groove 172 extending the longitudinal length of the staple support block, in an upwardly facing preferably planar surface of the staple support block 168, 168'. Longitudinal groove 172 is sized and has a shape respecting stapling base 164 so as to retain stapling base 164 in a releasable manner. Once the tissue fastening stapling function has been performed and the operating capsule is to be removed from the body, staples 104 pull easily out of longitudinal grooves 172 and remain within the stapled tissue which the staples have penetrated, thereby securing the stapled tissue together.

While staple support blocks 168 preferably are generally rectangular solid in configuration, adjoining member 170 preferably has an inclined lower surface designated generally 174.

A plurality of staple support members 166 are preferably housed within lower lip 28 of lower shell portion 24; an exemplary group of staple support members 166 is illustrated in FIG. 24. Each staple support block 168, 168' of a staple support member 166 is substantially vertically aligned with a respective preferably rectangular aperture 108 formed in planar upper surface 88 of lip 28 as illustrated in FIG. 23. Apertures 108 are preferably arranged in two parallel rows extending along the curved and then straight path traveled by ramp-knife assembly 50 as such path is defined by lower lip 28. Apertures in the inner row are denoted with a subscript "I" while apertures 108 in the outer row are, denoted with the subscript "O". Spacing of apertures $108_I$ and $108_O$ and specifically the longitudinal offset of apertures $108_I$ and $108_O$ corresponds to the longitudinal offset of respective staple support blocks 168, 168' of a single staple support member 166, with such offsets being best illustrated in the isometric view provided by FIG. 23.

Similar nomenclature is used to denote inner and outer staple support blocks 168 which are in registry with inner and outer apertures 108. Outer staple support blocks, in the outer row and which are aligned with apertures 1080, are denoted 1680. Staple support blocks which are in the inner row and are in registry with apertures $108_I$ are denoted $168_I$. This arrangement is illustrated in FIG. 23.

Referring specifically to FIG. 24, a section of lip portion 28 from lower shell portion 24 is depicted with the outer wall 102 substantially broken away to reveal the arrangement of staple support members 166 and the manner in which staple support members 166 are upwardly advanced by ramp-knife assembly 50 to effectuate tissue securement by stapling.

In FIG. 24 inner wall 96 of lower lip 28 has a surface 106 which is facing inwardly respecting the interior of lower lip 28 but faces outwardly respecting operating capsule 12 taken as a whole.

Surface 106 has a series of vertically extending channels formed therein, which are adapted for sliding receipt of a staple support block 168 of a staple support member 166. Only one of these channels, which has been designated 176 in FIG. 24, has been illustrated in FIG. 24, to aid drawing clarity. There is preferably one channel 176 for each staple support member 166.

Each channel 176 is defined by a rib 310, one of which has been illustrated in FIG. 23, extending transversely outwardly from surface 106, in a direction perpendicular to the plane of the paper in FIG. 24, and which extends along the entire vertical height of surface 106 in FIG. 24. Respective vertically extending longitudinally facing surfaces of two adjacent ones of these ribs are illustrated in dotted lines in FIG. 24 and are denoted 180; surface 180 of rib 310 appears as a line in FIG. 23.

At the end of each rib remote from surface 106 is a web which is parallel with surface 106. Two such webs have been illustrated in FIG. 24 and are designated generally 178; one web 178 is shown in FIG. 23 and has been broken away to illustrate the relationship between web 178 and a suture support block $168_I$ and specifically an oppositely longitudinally facing surface 181 thereof. The two dotted lines which denote the longitudinally facing transversely extending surfaces of rib 310, which surfaces are hidden by webs 178 in FIG. 24, are denoted 180 in FIG. 24. A longitudinally facing surface 180 of a rib 310 is longitudinally spaced from an immediately adjacent rib 310 a distance just slightly greater than the longitudinal length of a suture support block 168, as denoted by dimensional arrow L in FIG. 23. Hence, an inboard suture support block 168 of a suture support member 166 is slidably vertically movable in a groove defined by two adjacent ribs 310.

Webs 178 overlie longitudinally facing surfaces 180 of the ribs 310. Ribs 310 extend transversely outwardly respecting surface 96 a distance slightly greater than the thickness, in the transverse direction, of suture support block 168, which thickness is denoted by dimension T in FIG. 23. Since webs 178 overlie longitudinally facing surfaces 180 and since the ribs are slightly longer than the thickness of a suture support block 168, webs 178 serve to retain a suture support block in vertically sliding disposition within the groove defined by surface 106, rib 310 and web 178.

A portion of upper surface of lip 28 between inner apertures $108_I$ and outer apertures 108, defines a stop for suture support members 166 and is designated generally 182 in FIG. 23. This strip of preferably plastic material extends longitudinally and interferes with upper surfaces 184 of adjoining members 170 when suture support members 166 are urged sufficiently far upwardly within grooves defined by adjacent ribs 310. Hence, as ramp-knife assembly 50 urges the suture support members 166 vertically upwardly, sutures 104 may protrude through apertures 108 and upper portions of suture support blocks $168_I$, $168_O$ may similarly protrude through corresponding apertures $108_I$ and $108_O$. However, interference between adjoining member 170 of suture support member 166 and material strip 182 limits upward travel of the suture support member 166.

The suturing members have been illustrated as staples 104. While staples such as those illustrated as 104 are preferred, any suitable suturing means may be utilized in place of the staples illustrated as 104 in the drawings.

Still referring to FIG. 24, a plurality of outer staple support blocks $168_O$ forming portions of respective staple support members 166 are shown. For drawing clarity, an inner staple support block $168_I$ has been illustrated in dotted lines for only a single one of the staple support members 166. The staple support block $168_I$ shown in dotted lines is illustrated in position in the groove defined by the ribs 310 whose longitudinally facing surfaces are shown in dotted lines as 180.

Prior to contact by the ramp-knife assembly 50, which is illustrated in position generally to the left in FIG. 24, an individual staple support member 166 is positioned as illustrated by the staple support block $168_O$ at the extreme right hand side in FIG. 24. In such position, stapling fingers 262, 262' are straight and extend at substantially right angles from the upper surface of staple support block $168_O$.

As first cable 48 is drawn to the right in FIG. 24, first cable 48 pulls ramp-knife assembly 50 to the right in FIG. 24. As ramp-knife assembly 50 travels to the right in FIG. 24, the inclined ramp 82 is positioned directly under area 182 in planar upper surface 88 of lip 28, illustrated in FIGS. 18, 19 and 23, separating apertures $108_I$ from apertures $108_O$. Staple support members 166 are positioned with respective staple support blocks $168_I$, $168_O$ in registry with associated apertures $108_I$, $108_O$ and hence with each adjoining member 170 of a staple support member aligned with inclined ramp 82.

Inclined lower surfaces 174 of adjoining members 170 are preferably inclined at an angle corresponding to that of ramp 82. Hence, as ramp-knife assembly 50 is moved to the right in FIG. 24 by first cable 48, inclined ramp 82 contacts inclined lower surfaces 174 of adjoining members 170 and urges staple support members 166, of which adjoining members 170 are parts, vertically upwardly. This progressive vertically upward travel of staple support members 166, due to the horizontal travel of ramp-knife assembly 50, is illustrated in FIG. 24.

As travel of ramp-knife assembly 50 to the right in FIG. 24 pushes staple support members 166 vertically upwardly, stapling fingers 262, 262' associated therewith pass through an aperture 108 with which staple support block 168 carrying staple 104 is in registry and emerge from upper surface 88 of lower lip 28. As ramp-knife 50 continues further to the right in FIG. 24, ramp surface 82 continues to urge staple support members 166 vertically upwardly. Stapling fingers 262, 262' encounter anvil surfaces 260 which are formed in upper lip 26 of upper shell portion 22 and are illustrated in FIG. 24. As stapling fingers 262, 262' are urged against anvil surfaces 260, stapling fingers 262, 262' are bent and curve in a plane defined by the slot-like configuration of anvil surfaces 260. The curvature of stapling fingers 262, 262' in a plane defined by ramp-knife assembly 50 is shown by stapling fingers 262, 262' associated with the staple support block 1680 at the extreme left hand side of FIG. 24. The slot-like configuration of anvil surface 260 in upper lip 26 is illustrated in FIG. 26.

When tissue is present between lip portions 26 and 28 and stapling fingers 262, 262' of a staple are driven through such tissue and against anvil surfaces 260, the resulting curvature of stapling fingers 262, 262' illustrated in FIG. 24 after passage through the tissue located between lip portions 26 and 28 secures that tissue together. Due to the provision of outer and inner staple support blocks $168_O$, $168_I$ in registry with respective apertures $108_O$ and $108_I$, two parallel lines of staples or sutures securing together tissue results. The resulting securement of the tissue is illustrated by the dotted lines in FIG. 31.

Further respecting anvil surfaces 260, as illustrated in section in FIG. 26, anvil surfaces 260 are offset one from another with the curved downwardly facing portions of anvil surfaces 260 in upper lip 26 causing the resulting curve of stapling fingers 262, 262' in a direction back towards the direction in which stapling fingers 262, 262' extend away from stapling base 264, in a manner that the staples may be considered to curve back upon themselves thereby providing excellent securement together of tissue layers positioned between the two lips of the operating capsule.

Referring to FIGS. 2, 27 and 29 through 31, in the preferred embodiment of the apparatus the invention further includes means for grabbing tissue, specifically lumen wall tissue, and pulling that lumen wall tissue into operating capsule 12 so that the tissue may be cut and sutured thereby removing the diseased or otherwise undesirable tissue from the lumen wall. Two tissue grabbers are designated generally 194 in FIG. 2. While two such tissue grabbers have been illustrated and are preferred, it is to be understood that only a single tissue grabber may be provided or three or more tissue grabbers may be provided, depending on the size in which the apparatus is constructed and the particular conditions to be treated using the apparatus.

Each tissue grabber 194 preferably includes a handle member designated generally 196 where the handle member includes two preferably integrally formed finger rings 198 and a thumb ring 200. Each tissue grabber 194 further preferably includes a cable 202 where, similarly to the other cables described herein, cable 202 includes inner and outer portions denoted by subscripts "I" and "O" respectively; additionally, each cable 202 further includes an, intermediate portion denoted by subscript "M".

Thumb ring 200 is moveable axially relative to handle member 196 and specifically relative to finger rings 198 in the direction indicated by double-ended arrow TR in FIG. 2. Finger rings 198 are fixed to intermediate portion $202_M$ of cable 202. Thumb ring 200 is fixedly connected to inner portion $202_I$ of cable 200.

At the ends of cable 202 opposite from finger rings 198 and thumb ring 200, are two spring-loaded alligator clip-type members 204 which are connected to inner portion 202, of cable 202. Alligator clip-type members 204 have two facing, preferably metallic jaws, each having alligator-type teeth formed by serrations on the facing portion of the jaw. Each jaw is designated 206 in the drawings.

The spring-loading of jaws 206 of alligator clip-type members 204 results in jaws 206 opening as alligator clip-type members 204 are extended out of intermediate portions $202_M$ of cable 202. Such extension of alligator clip-type members 204 is effectuated by advancing the thumb ring 200 relative to finger rings 198 thereby to advance inner portion $202_I$ of cable 202 relative to intermediate portion $202_M$. Intermediate portion $202_M$ of cable 202 is preferably fabricated from material having excellent memory characteristics so that the physician or other attending health care professional can effectuate a desired bend of cable 202, specifically of intermediate portion $202_M$, and such bent intermediate portion $202_M$ will retain such bend as intermediate portion $202_M$ is advanced from or withdrawn into outer portion $202_O$ of cable 202. The desired bend may be introduced to intermediate portion $202_M$ manually prior to insertion of operating capsule 12 into the lumen of interest or may be effectuated during the operating procedure by advancing intermediate and inner portions of cable 202 until alligator clip-type members 204 contact one of the rigid interior surfaces of operating capsule 12. Once such contact has been effectuated, continued advancement of intermediate and inner portions $202_M$, $202_I$ of cable 202 will result in these portions of cable 202 bending. Due to the memory characteristic of intermediate portion $202_M$, the bend will remain in intermediate and inner portions $202_M$, $202_I$ of cable 22.

When the physician or other attending professional has positioned operating capsule 12 at the desired location within the lumen and has opened the operating capsule 12 thereby to provide access to the undesirable tissue to be removed, the lumen wall must be grasped and pulled into operating capsule 12 sufficiently far that all of the diseased or otherwise undesirable tissue is within operating capsule 12 prior to the tissue suturing and cutting operation. This tissue pulling is preferably effectuated using tissue grabbers 194. Specifically, the physician or other attending health care professional first preferably advances thumb rings 200 towards finger rings 198. This causes alligator clip-type members 204 at the ends of inner portion 202, to extend out of the intermediate portion $202_M$ of cable 202 with jaws 206 of alligator members 204 opening due to the spring-loading thereof. The physician or other attending health care professional then moves the alligator clip-type members, with jaws 206 open, into position to grasp the lumen wall tissue at the desired locations. This is accomplished by advancing finger ring 198 and thumb ring 200 together thereby advancing inner portion $202_I$ and intermediate portion $202_M$ of cables 202 and alligator clip-type members 204 all unitarily, without moving thumb ring 200 relative to finger ring 198.

Once the open jaws 206 of alligator clip-type members 204 are at the desired positions, the physician or other attending health care professional advances finger ring 198 away from thumb ring 200 while maintaining thumb ring 200 at a fixed position. This movement of finger ring 198, which would be to the left in FIG. 2, causes the intermediate portion $202_M$ of cable 202 to close about joined ends of jaws 206 of spring-loaded alligator clip-type members 204, thereby closing jaws 206 towards one another and entrapping tissue between the serrated jaws 206.

Once the tissue has been entrapped, the physician or other attending health care professional moves finger ring 198 and thumb ring 200 to the right in FIG. 2, without moving finger ring 198 relative to thumb ring 200. This effectively shortens the length of cables 202 which are within operating capsule 12 thereby drawing the gripped tissue into capsule 12. This is illustrated schematically in FIG. 31.

Once finger ring 198 and thumb ring 200 have been moved sufficiently far to the right in FIG. 2, without any relative motion therebetween, so as to draw the tissue into operating capsule 12 to the desired extent, the physician or other attending health care professional grasps and moves trigger 36 relative to handle 32. This advances ramp-knife assembly 50 along its path to the extent the operator moves trigger 36.

Advancement of ramp-knife assembly 50 along the path vertically advances staple support members 166 and staple support blocks 168, driving stapling fingers 262, 262' through tissue resting on planar upper surface 88 of lower lip 28. Due to the configuration of ramp-knife assembly 50 whereby ramp 82 effectuates vertical movement of staple support members 166 with ramp 82 preceeding knife portion 76 along the tissue, the tissue is stapled by the action of stapling fingers 262, 262' before being cut by knife portion 76.

Figure 31:
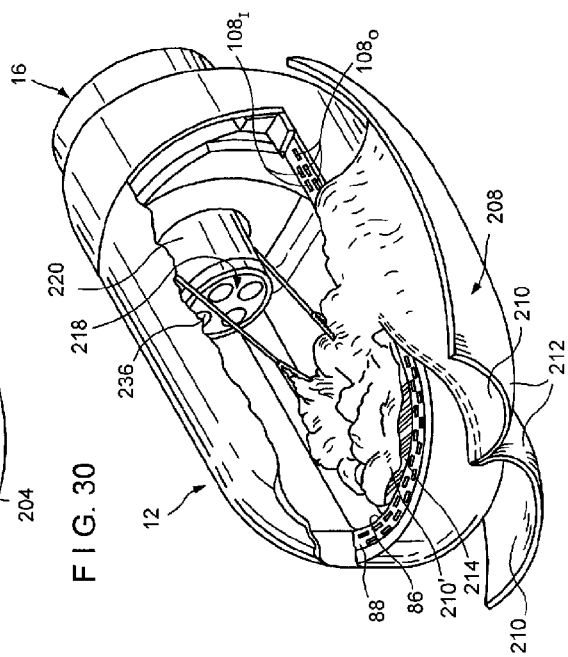
FIG. 31 is a partially broken isometric view of the operating capsule illustrated in FIGS. 1B, 2, 8, 9, 11, 12, 14, 15, 18, 28 and 30, showing grasp of malignant, diseased or otherwise undesired tissue to bring that tissue into the operating capsule interior and schematically illustrating tissue stapling and tissue cutting to resect the tissue within the operating capsule from surrounding healthy tissue.

Referring specifically to FIG. 31, lumenal wall tissue is designated generally 208. The inner surface of the lumenal wall which is a continuous interior surface prior to the tissue stapling and tissue cutting operations, is designated 210 while the outer surface of the lumenal wall is designated 212 in FIG. 31. The portion of the inner surface 210 of the lumenal wall tissue which has been grasped and drawn into operating capsule 12 is designated 210'.

In FIG. 31, configuration of the lumenal wall during the tissue stapling and cutting operation is shown. It is specifically to be noted that when using the apparatus of the invention and when practicing the methods of the invention, the lumenal wall may be drawn entirely into the operating capsule with lumenal wall tissue 208 folded upon itself as illustrated, so that when the lumenal wall tissue has, been drawn into the capsule, the exposed upper portion of tissue within operating capsule 12 and the exposed lower (or downwardly facing) portion of tissue within the capsule are both from inner surface 210 of the lumenal wall 208. The line denoting the lumenal wall tissue folded upon itself is designated 214 in FIG. 31.

One major advantage afforded by the apparatus and methods of the invention is that all of the tissue of the lumenal wall at a site of interest may be drawn into operating capsule 12 prior to the tissue suturing and cutting operation. As a result, once the tissue suturing and cutting operation is complete, an entire section of lumenal wall has been removed and is resident within the operating capsule. Where malignant tissue is being removed from a lumenal wall, this provides enhanced assurance that the resection of the tissue has successfully removed all of the malignant portion from the lumenal wall, as contrasted to techniques where only the inner surface of the wall is removed.

As is further apparent from FIG. 31, the tissue stapling function occurs prior to the tissue cutting function. This is evident from the fact that the two lines of staples, which have stapled together the folded-on-itself portion of the lumenal wall, are ahead of inclined leading tissue cutting edge 78 of knife portion 76.

As yet another advantage afforded by the invention, the stapling operation secures together healthy tissue in facing disposition along a site line removed from the line of tissue cutting. This results in faster healing at the wound site. Moreover, since tissue stapling is performed outboard of the locale at which tissue cutting is performed and since the diseased or other undesirable tissue is retained inboard of the tissue cutting function, the probability of contamination of healthy tissue (by the resected undesirable and possibly malignant tissue which remains within operating capsule 12) is minimized.

When apparatus 10 is used in performing procedures in the colon or even the small intestine, typically tip extremity 218 and flexible tubular transmission means 220 of endoscope 216 are fed through apparatus 10 from control module 14 and exit operating capsule 12 via an aperture 238 in upper shell portion 22 of operating capsule 12. Aperture 238 is illustrated in FIGS. 1B, 8, 9, 18 and 30.

Once endoscope 216 has been threaded through apparatus 10, if a procedure is being performed in the colon, tip extremity 218 and flexible tubular transmission means 220 of endoscope 216 are introduced into the colon via the rectum. The physician or other attending health care professional then proceeds, to guide tip portion 218 of endoscope 216 up the colon by manually advancing flexible tubular transmission means 220 into the rectum and controlling left/right and up/down movement of tip portion 218 using motion control disk 228 and motion control knob 230.

Once the physician or other attending health care professional has positioned tip portion 218 where the tissue of interest is in view and tip portion 218 is sufficiently close to that tissue that the tissue may be grasped and brought into the interior of operating capsule 12, the physician or other attending health care professional then advances operating capsule 12 and flexible tubular member 16 along flexible tubular transmission means 220, into the patient's colon via the rectum.

The physician guides operating capsule 12 up the colon and along flexible tubular transmission means 220 using directional control knobs 40 and 42 of control module 14. The physician continues to advance operating capsule 12 and flexible tubular member 16 until operating capsule 12 arrives at tip extremity 218, where the malignant, diseased or otherwise undesirable tissue to be resected is located.

Once operating capsule 12 is at this position, the physician withdraws flexible tubular transmission means slightly from apparatus 10 thereby withdrawing tip extremity 218 from aperture 238 into the position illustrated generally in FIG. 31 where tip extremity 218 is within operating capsule 12. With tip extremity 218 at this position, the physician or other attending health care professional proceeds to use tissue grabbers 194 to grasp the colon wall tissue, drawing the colon wall tissue including the malignant, other diseased or otherwise undesirable colon wall tissue into the interior of operating capsule 12, into a position generally illustrated in FIG. 31 where the malignant, other diseased or otherwise undesirable tissue is preferably entirely within the interior of operating capsule 12 and outer surface 212 of lumenal wall 208 is folded upon itself. Once the physician has manipulated the tissue into this position using tissue grabbers 194, the physician actuates ramp-knife assembly 50 to perform the stapling and tissue cutting functions as illustrated in FIG. 31.

Once tissue stapling and cutting has been performed, operating capsule 12 may be closed thereby to retain the malignant, other diseased or otherwise undesirable tissue in a position where it does not contact the remaining and presumably healthy lumenal wall tissue outside of operating capsule 12.

If desired, the physician may then advance tip extremity 218 and flexible tubular transmission means 220 of the endoscope 216 relative to apparatus 10 to cause tip extremity 218 to once again protrude from aperture 238. The physician may then slightly withdraw apparatus 10, specifically operating capsule 12 and flexible tubular member 16, thereby removing operating capsule 12 from the immediate vicinity of the wound site. This permits the physician to inspect the wound site using endoscope 16 by manipulating tip extremity 218 protruding out of aperture 238. If the endoscope 216 is equipped with cauterizing heaters and if cauterizing of the stapled wound is necessary to prevent any excessive bleeding, this may be performed using endoscope 216 and particularly tip extremity 218 protruding from aperture 238.

Once the surgical procedure has been completed and the physician is satisfied with the results, flexible tubular member 16 and operating capsule 12 are withdrawn from the colon. Flexible tubular transmission means 220 of endoscope 216 may be simultaneously withdrawn in a unitary motion with operating capsule 12 and flexible tubular member 16, or if further inspection of the wound site is desired, flexible tubular transmission means 220 of endoscope 216 may be removed from the colon after such further inspection has been performed.

While the foregoing description has discussed performing cauterization of the wound using endoscope 216, it is within the purview of the invention to provide separate cauterizing means as an accessory or an auxiliary item within operating capsule 12. Similarly, it is within the purview of the invention to provide multiple ports, such as aperture 238, for viewing the lumen interior where the surgical procedure is being performed.

Additionally, while the foregoing description has concentrated on use of an endoscope such as endoscope 216 illustrated generally in the drawings, it is within the purview of the invention to use apparatus 10 together with a colonoscope or an ectoscope or to use apparatus 10 in a catheter guided fashion.

Operating capsule 12 may be constructed in various shapes differing from that illustrated in the drawings. Particularly, operating capsule 12 may be constructed in the shape of a hemisphere of a football where the football has been divided in half along a vertical plane. In such case, aperture 238 might be provided at the point of the football.

Further respecting operating capsule 12, the opening between upper and lower shell portions 22, 24 need not be configured to be along the horizontal mid point of operating capsule 12.

Tissue grabbers 194 have been illustrated as including finger rings 198 and a thumb ring 200. Tissue grabbers 194 may equally well be provided with trigger-like means for controlling or actuating the tissue grabbers.

Further respecting tissue grabber means 194, while these means have been illustrated with alligator-like jaws, the tissue grabbing function could equally well be performed by suction cups with the necessary vacuum supplied via the endoscope.

While cables and pulleys have been illustrated to control the operating capsule, chains, ratchets and gears may also be used.

Referring to FIG. 32, an alternate embodiment of an operating capsule manifesting aspects of the invention is illustrated schematically where the operating capsule is designated generally 12'. In FIG. 32, the operating capsule is illustrated divided into two parts, 12'$_1$ and 12'$_2$. The apparatus illustrated schematically in FIG. 32 is configured to endolumenally remove a cylindrical wall section of undesired lumenal tissue and to circumferentially secure the remaining lumenal wall tissue from either side about the site of cylindrical removal.

Further respecting FIG. 32, a flexible tubular transmission means portion of a conventional endoscope is designated generally 220' and is illustrated schematically as including a tip extremity portion 218'.

Operating capsule 12' is configured generally cylindrically and, as illustrated, separates into two portions. Each portion of operating capsule 12' includes tissue grabbers, only the jaws of which have been illustrated schematically as 206' in FIG. 32.

The respective Cylindrical parts 12$_1$' and 12$_2$' have respective annular lips 27, 27' associated therewith. Lips 27, 27' are annular or circular and are made to be closely spaced one from another in a manner similar to upper and lower lips 26, 28 in the preferred embodiment of the apparatus described above. One of lips 27, 27' is equipped with tissue stapling or suturing and tissue cutting means of the same general type as illustrated in FIGS. 18 through 24, while the remaining one of lips 27, 27' is equipped with anvil surface means of the type generally illustrated in FIGS. 24 and 26. The tissue cutting means is preferably radially inboard of the tissue stapling or suturing means in lip 27 or 27'.

Further illustrated in FIG. 32 is a lumenal wall 208' which is generally cylindrical in configuration. As illustrated in FIG. 32, an annular or cylindrical portion 209 of lumenal wall tissue 208' has been drawn into a position at which cylindrical section 209 of lumenal wall tissue 208 is configured with a smaller diameter than lumenal wall tissue cylindrical portion 208'. As such, cylindrical lumenal wall portion 209 has a diameter sufficiently less than the diameter of operating capsule 12' that cylindrical lumenal wall portion 209 is completely within a cylindrical envelop defined by the interior of operating capsule 12'. Lumenal wall 208 is drawn into this position using tissue grabbers 206'.

Once lumenal wall 208' and cylindrical section thereof 209 are in the position illustrated in FIG. 32, the two parts 12'$_1$ and 12'$_2$ of operating capsule 12' are brought together to position lips 27, 27' in close proximity to one another. At this position, the tissue stapling or suturing means and tissue cutting means are actuated thereby suturing together circular or annular portions of lumenal wall denoted 350 which are trapped between lips 27, 27'. The stapling or suturing apparatus is configured to actuate all of the staples or sutures located around circular lip 27 or 27' simultaneously so that annular portions 350 of lumenal wall tissue are stapled or sutured together around the complete circle defined by lips 27, 27' at one time.

Once the tissue suturing or stapling and tissue cutting operations have been performed, cylindrical section 209 of lumenal wall tissue 208 is retained within operating capsule 12' whereupon operating capsule 12' is removed from the lumen. The lumenal wall tissue remains, having had a cylindrical section removed therefrom, with an annular, 360° line of suturing or staples securing together portions of cylindrical lumenal wall 208' from which cylindrical wall section 209 has been removed.

Operation of operating capsule portions 12'$_1$ and 12'$_2$ is effectuated using cables, an operating control module and a flexible cable carrying member such as illustrated in FIGS. 1 through 31. A radially foreshortened version of flexible cable carrying member 16 may be provided about endoscope 220', between operating capsule sections 12'$_1$ and 12'$_2$, to carry cables between the two sections 12'$_1$ and 12'$_2$ of the operating capsule 12' in order to close cylindrical sections 12'$_1$ and 12'$_2$ of the operating capsule 12' upon one another to bring lips 27, 27' into proximity with one another, to be in position to effectuate the tissue securement and cutting functions.

While the preferred embodiments of the invention have been described above and alternative embodiments have also been described, the scope of protection to which the invention is believed entitled is defined by the claims and by equivalents thereto which perform substantially the same function in substantially the same way to achieve substantially the same result as set forth in the claims, so long as such substantial equivalents, as defined by a claim for such substantial equivalent, do not read on the prior art.

I claim the following:

1. An apparatus for performing an intralumenal procedure, comprising:
   an endoluminal operating capsule comprising a first shell, a second shell and a plurality of staple receiving slots formed in a lip extending along a first longitudinally elongated wall of the first shell and a staple advancement member movable along the lip, for driving staples from the staple receiving slots through tissue positioned adjacent thereto, wherein the capsule is configured so that the staples are driven out of the capsule at an angle with respect to a longitudinal axis of the capsule, the longitudinal axis extending from a proximal end to a distal end of the capsule, the capsule further comprising a hinged portion extending along a second longitudinally elongated wall of the first shell and configured so that the first shell is rotatable relative to the second shell about an axis substantially parallel to the longitudinal axis of the capsule;
   a control handle remaining outside the body for receiving tactile motions of an operator corresponding to a desired positioning of the capsule;
   first and second substantially coaxial flexible sheaths extending from the capsule to the control handle;
   first and second control wires extending in an annular space between the first and second sheaths from the capsule to the control handle to transmit forces from the control handle to the capsule; and
   a coupling between the first and second sheaths maintaining the first and second control wires in a circumferentially spaced relation to one another so that force transmitted by the control wires follows a desired path and limits a degree of bending of the first and second sheaths within a desired range.

2. The apparatus of claim 1, wherein the coupling between the first and second sheaths includes a plurality of serially engaging disks, each disk further comprising a substantially conical central portion having an axial aperture therein extending around the first sheath and an annular flange at a base of the conical portion including a plurality of radial apertures extending radially inward from a periphery of the flange, an exterior of the conical portion extending through an annular flange and fitting into a hollow conical portion of an adjacent disk.

3. An apparatus for performing an intralumenal procedure on a lumen wall of a lumen, comprising:
   an endoluminal operating capsule comprising a first shell, a second shell and a plurality of staple receiving slots formed in a lip extending along a first longitudinally elongated wall of the first shell and a staple advancement member movable along the lip, for driving staples from the staple receiving slots through tissue positioned adjacent thereto, wherein the capsule is configured so that the staples are driven out of the capsule at an angle with respect to a longitudinal axis of the capsule, the longitudinal axis extending from a proximal end to a distal end of the capsule, the capsule further comprising a hinged portion extending along a second longitudinally elongated wall of the first shell and configured so that the first shell is rotatable relative to the second shell about an axis substantially parallel to the longitudinal axis of the capsule;
   a control module which remains outside the body for receiving tactile motions of an operator to generate signals indicative of a desired positioning of the capsule;
   first and second substantially coaxial flexible sheaths extending from the capsule to the control module;
   first and second control wires extending in an annular space between the first and second sheaths from the capsule to the control module, the first and second control wires positioning the capsule along and within a body lumen by transmitting forces applied manually thereto via the control module along a curvilinear path as the first and second sheaths bend to define the curvilinear path while limiting curvilinear bending of the first and second sheaths to a preselected degree; and
   a coupling between the first and second sheaths maintaining the first and second control wires in circumferentially spaced relation to one another so that force transmitted by the control wires follows a desired path to limit a degree of bending of the first and second sheaths within a desired range.

4. A surgical device, comprising:
   an operating capsule, the operating capsule including a first shell, a second shell, and a staple assembly, wherein the capsule is configured so that staples extend out of a first longitudinally elongated wall of the first shell at an angle with respect to a longitudinal axis of the capsule, the longitudinal axis extending from a proximal end to a distal end of the capsule, the capsule further comprising a hinged portion extending along a second longitudinally elongated wall of the first shell and configured so that the first shell is rotatable relative to the second shell about an axis substantially parallel to the longitudinal axis of the capsule;
   a control module; and
   a flexible tube having a distal end and a proximal end, wherein the distal end is connected to the operating capsule and the proximal end is connected to the control module, the flexible tube including an outer sheath; and
   a plurality of disks disposed within the outer sheath, each of the disks being substantially conical and including an inner aperture extending therethrough.

5. The surgical device according to claim 4, wherein each of the plurality of disks includes a convex exterior surface and a hollow concave interior.

6. The surgical device according to claim 5, wherein the flexible tube further includes an inner sheath at least partly disposed within the inner apertures of the disks.

7. A surgical device, comprising:
an operating capsule, the operating capsule comprising a first shell, a second shell and a staple assembly wherein the capsule is configured so that staples extend out of a first longitudinally elongated wall of the first shell at an angle with respect to a longitudinal axis of the capsule, the longitudinal axis extending from a proximal end to a distal end of the capsule, the capsule further comprising a hinged portion extending along a second longitudinally elongated wall of the first shell and configured so that the first shell is rotatable relative to the second shell about an axis substantially parallel to the longitudinal axis of the capsule;
a control module;
a flexible tube having a distal end and a proximal end, wherein the distal end is connected to the operating capsule and the proximal end is connected to the control module, the flexible tube including an outer sheath; and
a control wire disposed within the flexible tube, a proximal end of the control wire being connected to the control module with a distal end of the control wire connected to the operating capsule, the control module actuating the staple assembly via the control wire.

8. The surgical device according to claim 7, wherein the flexible tube includes an outer sheath and a plurality of disks disposed within the outer sheath, the control wire being disposed within the outer sheath.

9. The surgical device according to claim 8, wherein each of the plurality of disks is shaped substantially as a hollow cone having an inner aperture extending therethrough.

10. A surgical device, comprising:
an operating capsule including a first shell, a second shell and a staple assembly and at least one tissue clip, wherein the capsule is configured so that staples extend out of a first longitudinally elongated wall of the first shell at an angle with respect to a longitudinal axis of the capsule, the longitudinal axis extending from a proximal end to a distal end of the capsule, the capsule further comprising a hinged portion extending along a second longitudinally elongated wall of the first shell and configured so that the first shell is rotatable relative to the second shell about an axis substantially parallel to the longitudinal axis of the capsule;
a control module; and
a flexible tube having a distal end connected to the operating capsule and a proximal end connected to the control module, the flexible tube including an outer sheath and a plurality of disks disposed within the outer sheath, each of the plurality of disks being shaped substantially as a hollow cone including an inner aperture extending therethrough.

11. The surgical device according to claim 10, wherein each of the plurality of disks includes a convex exterior surface and a concave interior surface.

12. The surgical device according to claim 11, wherein the flexible tube further includes an inner sheath at least partly disposed within the inner apertures of the disks.

13. A surgical device, comprising:
an operating capsule, the operating capsule including a first shell, a second shell and a staple assembly and at least one tissue clip wherein the capsule is configured so that staples extend out of a first longitudinally elongated wall of the first shell at an angle with respect to a longitudinal axis of the capsule, the longitudinal axis extending from a proximal end to a distal end of the capsule, the capsule further comprising a hinged portion extending along a second longitudinally elongated wall of the first shell and configured so that the first shell is rotatable relative to the second shell about an axis substantially parallel to the longitudinal axis of the capsule;
a control module;
a flexible tube having a distal end connected to the operating capsule and a proximal end connected to the control module;
a control wire disposed within the flexible tube, a proximal end of the control wire being connected to the control module and a distal end of the control wire being connected to the operating capsule so that the control module actuates the staple assembly via the control wire; and
a clip cable disposed within the flexible tube, a proximal end of the clip cable being connected to the control module and a distal end of the clip cable being connected to the tissue clip so that the control module actuates the tissue clip via the clip cable.

14. The surgical device according to claim 13, wherein the flexible tube includes an outer sheath and a plurality of disks disposed within the outer sheath, the control wire and clip cable being disposed within the outer sheath.

15. The surgical device according to claim 14, wherein each of the plurality of disks is shaped substantially as a hollow cone having an inner aperture extending therethrough.

* * * * *